(12) United States Patent
Johnson

(10) Patent No.: US 6,649,172 B2
(45) Date of Patent: Nov. 18, 2003

(54) AMPHIPATHIC ALDEHYDES AND THEIR USES AS ADJUVANTS AND IMMUNOEFFECTORS

(75) Inventor: David A. Johnson, Hamilton, MT (US)

(73) Assignee: Corixa Corporation, Seattle, WA (US)

( * ) Notice: Subject to any disclaimer, the term of this patent is extended or adjusted under 35 U.S.C. 154(b) by 79 days.

(21) Appl. No.: 09/810,915

(22) Filed: Mar. 16, 2001

(65) Prior Publication Data

US 2001/0053363 A1 Dec. 20, 2001

Related U.S. Application Data

(60) Provisional application No. 60/190,466, filed on Mar. 17, 2000.

(51) Int. Cl.[7] ............... A61K 39/39; A61K 39/155; A61K 39/29; A61K 39/02; A01N 43/16; C07H 15/203; C07C 69/773; C07C 59/92

(52) U.S. Cl. ................. 424/278.1; 424/204.1; 424/206.1; 424/227.1; 424/234.1; 424/277.1; 514/25; 536/18.2; 560/53; 562/463

(58) Field of Search ............ 424/278.1, 227.1, 424/206.1, 234.1, 204.1, 277.1; 536/18.2; 560/53; 562/463; 514/25

(56) References Cited

U.S. PATENT DOCUMENTS

| | | | |
|---|---|---|---|
| 4,410,537 A | 10/1983 | Kneen | |
| 4,535,183 A | 8/1985 | Kneen | |
| 5,508,310 A | * 4/1996 | Rhodes | |
| 5,599,974 A | 2/1997 | Abraham et al. | |
| 5,872,151 A | * 2/1999 | Rhodes | |

OTHER PUBLICATIONS

Abstract of PGPUB–Document No. US 20020146828 A1 (2002).*

Merriam–Webster Collegiate Dictionary, Tenth Edition (1996), p. 29, Merriam–Webster, Inc.*

Wagner, R. et al., "Synthesis of Porphyrins Tailored with Eight Facially–Encumbering Groups. An Approach to Solid–State Light–Harvesting Complexes" *Tetrahedron* vol. 50, No. 38, pp. 11097–11112, (1994) Great Britain.

Weintraub, J.et al., "Synthesis of Unsymmetrically Branched Dendrimeric Wedges up to the Fourth Generation Based on 2,3–Dihydroxybenzyl Alcohol." *J. Org. Chem.*, vol. 64, No. 11, (1999).

* cited by examiner

*Primary Examiner*—Mary E. Ceperley
(74) *Attorney, Agent, or Firm*—Townsend and Townsend and Crew LLP

(57) ABSTRACT

This invention relates to novel aldehyde containing compounds and their uses as adjuvants and immunoeffectors.

27 Claims, No Drawings

AMPHIPATHIC ALDEHYDES AND THEIR USES AS ADJUVANTS AND IMMUNOEFFECTORS

CROSS-REFERENCES TO RELATED APPLICATIONS

This application claims priority to U.S. Provisional Patent Application Serial No. 60/190,466 filed on Mar. 17, 2000, the disclosure of which is incorporated herein in its entirety for all purposes.

BACKGROUND OF THE INVENTION

The only vaccine adjuvant currently licensed for human use in the United States is alum, (see, Arnon and Regenmortel, *FASEB J.* 1992, 6: 3265–3272) a group of aluminum salts which enhance humoral (antibody) immunity to vaccine antigens (Arnon and Regenmortel, 1992; Edelman, *Rev. Infect. Dis.* 1980, 2: 370–383). The recognition that cell-mediated (thymus or T-cell) immune responses—particularly the induction of T-helper type 1 (Th-1) cells and cytotoxic T-lymphocytes (CTLs)—are crucial for generating protective immunity against many infectious agents has prompted efforts to discover new vaccine adjuvants which augment both antibody and T-cell responses (Arnon and Regenmortel, 1992).

The adjuvant properties of saponin were first recognized in France in the 1930's. (see, Bomford et al., *Vaccine* 1992, 10: 572–577). Two decades later the saponin from the bark of the *Quillaja saponaria* Molina tree found wide application in veterinary medicine, but the variability and toxicity of these crude preparations precluded their use in human vaccines. (see, Kensil et al., *In Vaccine Design: The Subunit and Adjuvant Approach;* Powell, M. F., Newman, J. J., Eds.; Plenum Press: New York, 1995 pp. 525–541).

In the 1970's a partially purified saponin fraction known as Quil A was shown to give reduced local reactions and increased potency (see, Kensil et al., 1995). Further fractionation of Quil A, which consisted of at least 24 compounds by HPLC, demonstrated that the four most prevalent saponins, QS-7, QS-17, QS-18, and QS-21, were potent adjuvants (see, Kensil, C. R. *Crit Rev. Ther. Drug Carrier Syst.* 1996, 13, 1–55; Kensil et al., 1995). QS-21 and QS-7 were the least toxic of these. Partly because of its reduced toxicity, highly purified state (though still a mixture of no less than four compounds), (see, Soltysik, S.; Bedore, D. A.; Kensil, C. R. Ann. *N.Y. Acad. Sci.* 1993, 690: 392–395) and more complete structural characterization, QS-21 (3) was the first saponin selected to enter human clinical trials. (see, Kensil, 1996; Kensil et al., 1995).

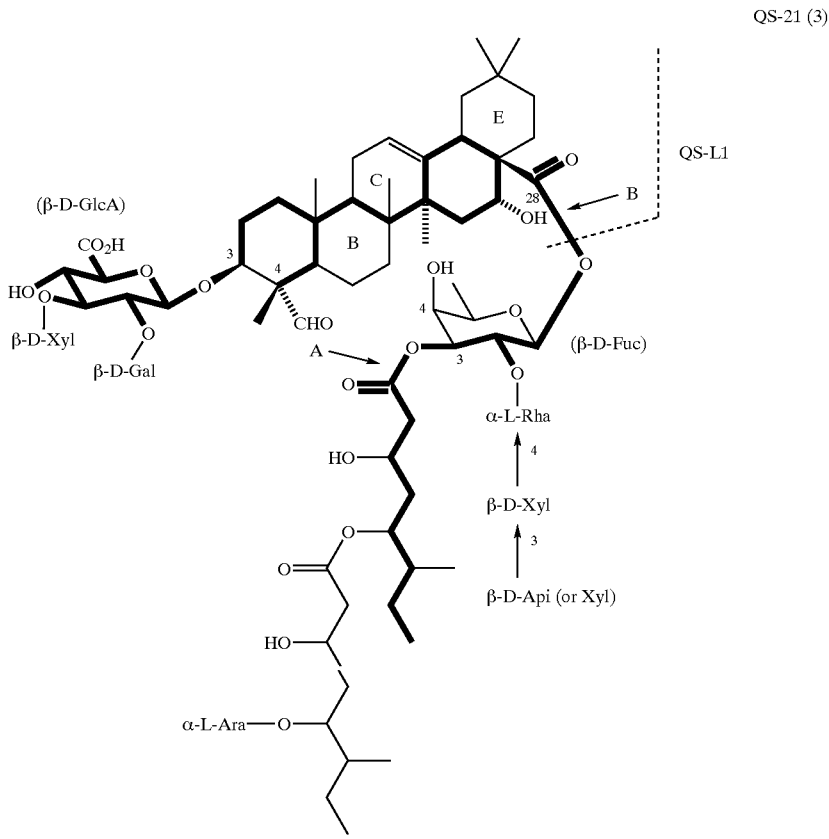

QS-21 and other Quillaja saponins increase specific immune responses to both soluble T dependent and T-independent antigens, promoting an Ig subclass switch in B-cells from predominantly IgG1 or IgM to the IgG2a and IgG2b subclasses (Kensil et al., 1995). The IgG2a and IgG2b isotypes are thought to be involved in antibody dependent cellular cytotoxicity and complement fixation (Snapper and Finkelman, *In Fundamental Immunology,* 4th ed.; Paul, W. E., Ed.: Lippincott-Raven: Philadelphia, Pa., 1999, pp. 831–861). These antibody isotypes also correlate with a Th-1 type response and the induction of IL-2 and IFN-γ-cytokines which play a role in CTL differentiation and maturation (Constant and Bottomly, *Annu. Rev. Immunology* 1997, 15: 297–322). As a result, QS-21 and other Quillaja saponins are potent inducers of class I MHC-restricted CD8+ CTLs to subunit antigens (Kensil, 1996; Kensil et al., 1995).

The mechanisms of saponin action have been investigated both by chemical modification of QS-21 and other saponins and by assessing the adjuvant activity of structurally diverse saponins (see, Bomford et al., *Vaccine* 1992, 10: 572–577; Soltysik et al., *C. R. Vaccine* 1995, 13: 1403–1410; Kensil et al., *Adv. Exp. Med. Biol.* 1996, 404: 165–172; Kensil et al., *J. Dev. Biol. Stand.* 1998, 92: 41–47). As the name suggests, saponins are surface-active adjuvants due to their amphipathic structure and ability to form micelles in solution. While micelle formation does not appear essential to saponin adjuvanticity, QS-21 may promote CD8+ CTL responses by associating with and disrupting the cell surface of antigen-presenting cells (APCs) and directing soluble antigen into the cytoplasm (Kensil, 1996). The importance of the complex fatty acid domain of QS-21 for CTL activity is not clear as hydrophilic saponins also induce cell-mediated responses (see, Kensil et al., 1998; So et al., *Mol. Cells* 1997, 7: 178–186).

An important structural feature for saponin adjuvanticity appears to be the formyl group at C-4 of

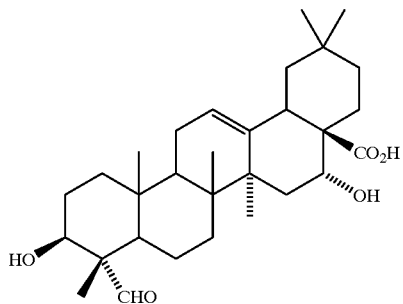

Quillaic Acid (1)

Blocking the aldehyde of QS-21 or reducing it to an alcohol abolishes adjuvant activity, (see, Soltysik et al., 1995) suggesting that Schiff base formation (the reversible reaction of an aldehyde with an amine to form an imine: $RCHO+RNH_2 \rightarrow RCH=NR$) is important to saponin adjuvanticity. Since saponins are effective adjuvants with hydrophilic polysaccharides lacking amino groups, (Kensil, 1996), Schiff base formation with cells of the immune system is likely. Indeed, Schiff base formation is thought to play an important role in APC-T-cell interactions and appears to be a critical determinant of the immunopotentiating ability of the zenobiotic tucaresol and other amphipathic aldehydes (see, Rhodes, *Immunol. Today* 1996, 17: 436–441; Hazen et al., *J. Biol. Chem.* 1997, 272: 16990–16998). Amphipathic aldehydes can substitute for the carbonyl groups constitutively expressed on APCs by forming a Schiff base with CD4+ T-cell surface amines and providing a costimulatory signal which leads to a Th-1 type profile of cytokine production and the enhancement of MHC class I-restricted CTL responses (Rhodes, 1996).

Potent, low-toxicity adjuvants which drive both effector arms of the immune system are needed to improve the safety and efficacy of existing vaccines and potentiate the weak immunogenicity of nascent synthetic vaccines. The present invention fulfills the aforementioned and other needs.

SUMMARY OF THE INVENTION

In one aspect, the present invention provides a compound represented by the Formula I:

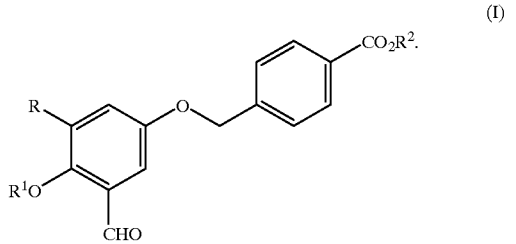

(I)

In Formula I, the symbol R represents hydrogen or —C(O)H. The symbol $R^1$ represents a member selected from hydrogen, a substituted $C_{1-20}$ alkyl group, an unsubstituted $C_{1-20}$ alkyl group, a saccharyl group, and a group represented by the formula —C(O)—[C($R^3$)($R^4$)]$_n$—COOH or —[C($R^3$)($R^4$)]$_n$—COOH, wherein each $R^3$ and $R^4$ independently is a member selected from hydrogen, a substituted $C_{1-10}$ alkyl group, an unsubstituted $C_{1-10}$ alkyl group. The symbol n represents an integer from 1 to 5. The symbol $R^2$ represents a member selected from hydrogen, a substituted $C_{1-20}$ alkyl group, an unsubstituted $C_{1-20}$ alkyl group, and a group represented by the formula —$(CH_2)_m$CH(OH)$(CH_2)_p$O$R^5$, wherein m and p are independently 1 or 2, and $R^5$ is a $C_{2-20}$ acyl group, or a group represented by the formula

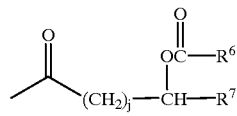

wherein j is an integer from 1 to 5, and $R^6$ and $R^7$ are independently selected from the group of hydrogen, a substituted $C_{1-20}$ alkyl group, and an unsubstituted $C_{1-20}$ alkyl group; or a pharmacologically acceptable salt thereof.

In a second aspect, the present invention provides a liposome vesicle comprising a compound of Formula I.

In a third aspect, the present invention also provides a compound comprising an antigen covalently linked to a compound according to Formula I.

In a fourth aspect, the present invention also provides a vaccine composition comprising an antigen and a compound of Formula I.

In a fifth aspect, the present invention also provides an adjuvant composition for potentiating the immunogenicity of an antigen, including a suspension of water or an aqueous solution. The suspension or solution includes a compound according to Formula I.

The present invention also provides a method for inducing or enhancing immunogenicity of an antigen in a mammal. The method includes administering to the mammal a vaccine composition that includes the antigen and a vaccine adjuvant composition that includes an effective immunopotentiatory amount of a compound according to Formula I.

In a seventh aspect, the present invention also provides a method for treating or preventing a disease in a mammal. The method includes administering to the mammal a vaccine composition. The vaccine composition includes an antigen and an effective immunopotentiatory amount of a compound according to Formula I.

The present invention also provides methods for preparing adjuvants or immunoeffectors. The method includes contacting a first compound with a second compound, thereby forming a third compound under conditions sufficient to form a third compound or a pharmacologically acceptable salt thereof.

The first compound has the formula:

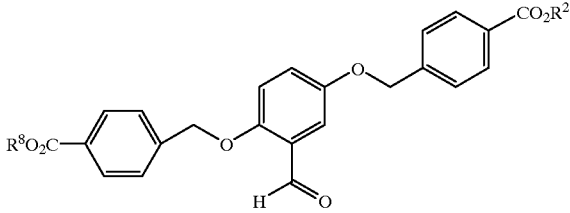

wherein $R^2$ and $R^8$ are independently selected from the group of hydrogen, a substituted $C_{1-20}$ alkyl group, an unsubstituted $C_{1-20}$ alkyl group, and a group having the formula $—(CH_2)_m CH(OH)(CH_2)_p OR^5$. The symbols m and p are independently 1 or 2. The symbol $R^5$ represents a member selected from the group of s substituted $C_{2-20}$ acyl group, an unsubstituted $C_{2-20}$ acyl group, or a group having the formula:

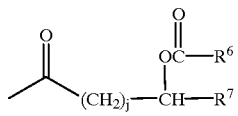

wherein j is an integer from 1 to 5. The symbols $R^6$ and $R^7$ are independently selected from the group of hydrogen, a substituted $C_{1-20}$ alkyl group, and an unsubstituted $C_{1-20}$ alkyl group.

The second compound is selected from the group of $MX_n$. The symbol M represents a member selected from the group of $Al^{3+}$, $As^{3+}$, $B^{3+}$, $Fe^{2+}$, $Fe^{3+}$, $Ga^{3+}$, $Mg^{2+}$, $Sb^{3+}$, $Sb^{5+}$, $Sn^{2+}$, $Sn^{4+}$, $Ti^{2+}$, $Ti^{3+}$, $Ti^{4+}$, and $Zn^{2+}$. The symbol n is an integer from 2 to 5, $MgX_2$—$OEt_2$, $BX_3 \cdot SMe_2$, $Et_2AlCl$, $EtAlCl_2$. The symbol X represents a member selected from the group of Cl, I, F, and Br. Alternatively, MXn represents a member selected from the group of monoalkyl boronhalides, dialkyl boronhalides, and monoaryl boronhalides, diaryl boronhalides.

The third compound has a structure according to the formula below:

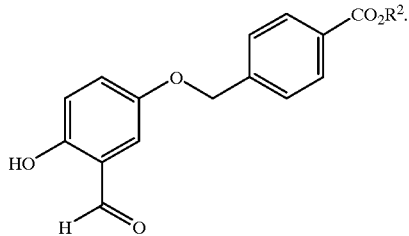

Other objects, features and advantages of the present invention will be apparent from the detailed description that follows

DETAILED DESCRIPTION OF THE INVENTION AND THE PREFERRED EMBODIMENTS

Definitions

The term "acyl" refers to those groups derived from an organic acid by removal of the hydroxy portion of the acid. Accordingly, acyl is meant to include, for example, acetyl, propionyl, butyryl, decanoyl, pivaloyl, benzoyl and the like. A "$C_1$–$C_{20}$ acyl group" is an acyl group having from 1 to 20 carbons.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$–$C_{10}$ means one to ten carbons). Examples of saturated hydrocarbon radicals include groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below as "heteroalkyl." Alkyl groups, which are limited to hydrocarbon groups are termed "homoalkyl".

A "$C_1$–$C_{20}$ alkyl group" is a substituted or unsubstituted alkyl group having from 1 to 20 carbons. Similarly, a "$C_{11}$ alkyl group" is a substituted or unsubstituted alkyl group having 11 carbons.

The term "alkylene" by itself or as part of another substituent means a divalent radical derived from an alkane, as exemplified by $—CH_2CH_2CH_2CH_2—$, and further includes those groups known as "heteroalkylenes."

The term "alkylene" by itself or as part of another substituent means a divalent radical derived from an alkane, as exemplified by $—CH_2CH_2CH_2CH_2—$, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include $—CH_2—CH_2—O—CH_3$, $—CH_2—CH_2—NH—CH_3$, $—CH_2—CH_2—N(CH_3)—CH_3$, $—CH_2—S—CH_2—CH_3$, $—CH_2—CH_2$, $—S(O)—CH_3$, $—CH_2—CH_2—S(O)_2—CH_3$, $—CH=CH—O—CH_3$, $—Si(CH_3)_3$, $—CH_2—CH=N—OCH_3$, and $—CH=CH—N(CH_3)—CH_3$. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified by —CH$_2$—CH$_2$—S—CH$_2$CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo (C$_1$–C$_4$)alkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon substituent, which can be a single ring or multiple rings (up to three rings) which are fused together or linked covalently. The term "heteroaryl" refers to aryl groups (or rings) that contain from zero to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and acyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NRR'R")=NR'", —NR'C(NR'R")=NR'", —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R" and R'" each independently refer to hydrogen, and heteroalkyl, unsubstituted aryl, aryl substituted with 1–3 halogens, unsubstituted alkyl, alkoxy or thioalkoxy groups, or aryl-(C$_1$–C$_4$)alkyl groups. When a compound of the invention includes more than one R group, for example, each of the R groups is independently selected as are each R', R" and R'" groups when more than one of these groups is present. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. From the above discussion of substituents, one of skill in the art will understand that the term "alkyl" is meant to include groups such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similarly, substituents for the aryl and heteroaryl groups are varied and are selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R'", —NR—C(NR'R")=NR'", —NRC(NR'R")=NR'", —NR—C(NR'R")=NR'", —S(O)R', —S(O)$_2$R', —S(O)$_2$NR'R", —NRS(O)$_2$R', —N$_3$, —CH(Ph)$_2$, fluoro(C$_1$–C$_4$)alkoxy, and fluoro(C$_1$–C$_4$)alkyl, in a number ranging from zero to the total number of open valences on the aromatic ring system; and where R', R" and R'" are independently selected from hydrogen, (C$_1$–C$_8$)alkyl and heteroalkyl, unsubstituted aryl and heteroaryl, (unsubstituted aryl)-(C$_1$–C$_4$)alkyl, and (unsubstituted aryl) oxy-(C$_1$–C$_4$)alkyl. When a compound of the invention includes more than one R group, for example, each of the R groups is independently selected as are each R', R" and R'" groups when more than one of these groups is present.

Two of the substituents on adjacent atoms of the aryl or heteroaryl ring may optionally be replaced with a substituent of the formula —T—C(O)—(CRR'$_2$)$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula —A—(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R'")$_t$—, where s and t are independently integers of from 0 to 3, and X is —O—, —NR'—, —S—, —S(O)—, —S(O)$_2$—, or —S(O)$_2$NR'—. The substituents R, R', R" and R'" are independently selected from hydrogen or unsubstituted (C$_1$–C$_6$)alkyl.

As used herein, the term "heteroatom" is meant to include oxygen (O), nitrogen (N), sulfur (S) and silicon (Si).

The term "saccharyl" refers to those groups derived from a sugar, a carbohydrate, a saccharide, a disaccharide, an oligosaccharide, or a polysaccharide molecule by removal of a hydrogen or a hydroxyl group. Accordingly, saccharyl groups (e.g., glucosyl, mannosyl, etc.) can be derived from molecules that include, but are not limited to, glucuronic acid, lactose, sucrose, maltose, allose, alltrose, glucose, mannose, idose, galactose, talose, ribose, arabinose, xylose, lyxose, threose, erythrose, β-D—N-Acetylgalactosamine, β-D—N-Acetylglucosamine, fucose, sialic acid, etc. A "$C_6$–$C_{20}$ saccharyl group" is a substituted (e.g. acylated saccharyl, alkylated saccharyl, arylated saccharyl, etc.) or unsubstituted saccharyl group having from 6 to 20 carbons. An example of a saccharyl group is a radical formed by the removal of the hydroxyl on the C1 position of glucuronic acid as represented by the formula:

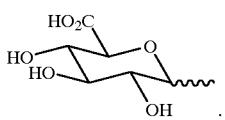

The wavy bond indicates where the glucuronide radical (i.e., a glucuronic acid group) would be attached to another substituent, e.g., an aglycon unit. Thus, saccharyl groups include sugar molecules where the hydroxyl on the C1 position has been removed.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science, 1977, 66, 1–19). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention. The chemical compounds of the present invention may exist in (+) and (−) forms as well as in racemic forms.

Racemic forms can be resolved into the optical antipodes by known methods and techniques. One way of separating the racemic forms is exemplified by the separation of racemic amines by conversion of the racemates to diastereomeric salts of an optically active acid. The diastereomeric salts are resolved using one or more art recognized methods. The optically active amine is subsequently liberated by treating the resolved salt with a base. Another method for resolving racemates into the optical antipodes is based upon chromatography on an optical active matrix. Racemic compounds of the present invention can thus be resolved into their optical antipodes, e.g., by fractional crystallization of d- or l-tartrates, -mandelates, or -camphorsulfonate) salts for example.

The chemical compounds of the present invention may also be resolved by the formation of diastereomeric amides by reaction of the chemical compounds of the present invention with an optically active carboxylic acid such as that derived from (+) or (−) phenylalanine, (+) or (−) phenylglycine, (+) or (−) camphanic acid or the like. Alternatively, the compounds of the invention are resolved by the formation of diastereomeric carbamates by reaction of the chemical compound of the present invention with an optically active chloroformate or the like.

Additional methods for the resolving the optical isomers are known in the art. Such methods include those described by Collet and Wilen, ENANTIOMERS, RACEMATES, AND RESOLUTIONS, John Wiley and Sons, New York (1981). Moreover, some of the chemical compounds of the invention can exist in syn- and anti-forms (Z- and E-form), depending on the arrangement of the substituents around a double bond. A chemical compound of the present invention may thus be the syn- or the anti-form (Z- and E-form), or it may be a mixture hereof.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are intended to be encompassed within the scope of the present invention.

An "effective immunopotentiatory amount" is an amount of a compound that is effective to potentiate an immune response to one or more antigens. The immune response can be measured, without limitation, by measuring antibody titers against an antigen (e.g., HBsAg, etc.), assessing the ability of a vaccine containing a compound of the present invention to immunize a host in response to a disease or antigen challenge, etc. Preferably administering an "effective immunopotentiatory amount" of a compound of formula I to a subject increases one or more antibody titers (e.g., IgG1, IgG1, IgG2a, IgG2b, etc.) by 10% or more over a nonimmune control, even more preferably by 20% or more over a nonimmune control, and still more preferably by 30% or more over a nonimmune control, and most preferably by 100% or more over a nonimmune control.

Introduction

In an effort to improve the safety of vaccines, manufacturers are avoiding whole cell killed vaccines, and producing recombinant or subunit vaccines. In the preparation of these safer vaccines extraneous bacterial or viral components are eliminated, while the minimal structures or epitopes deemed necessary for protective immunity remain. The safety of these vaccines is improved due to the elimination of extraneous bacterial or viral components which often times prove to be toxic and pyrogenic. However, the same components that result in toxicity provide nonspecific immunostimulation that make whole cell vaccines so effective. Without the additional immunostimulation the minimal structures and epitopes comprising recombinant and subunit vaccines are often poorly immunogenic. Thus, the need for effective vaccine adjuvants is well recognized. Ideally, these adjuvants will boost the protective immune response without inducing unwanted toxicity and pyrogenicity.

In an effort to obtain novel immunostimulants, synthetic molecules have been prepared which share structural similarities with the immunoeffector tucaresol. These compounds and methods for using them are described in more detail below.

Compounds

In one aspect, the present invention provides a compound represented by the Formula I:

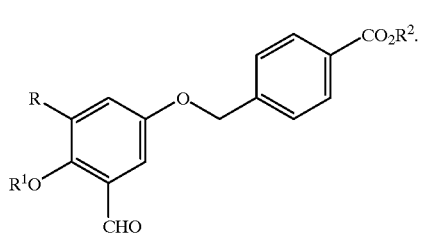

In Formula I, the symbol R represents hydrogen or —C(O)H. The symbol $R^1$ represents a member selected from hydrogen, a substituted $C_{1-20}$ alkyl group, an unsubstituted $C_{1-20}$ alkyl group, a saccharyl group, and a group represented by the formula —C(O)—[C($R^3$)($R^4$)]$_n$—COOH or —[C($R^3$)($R^4$)]$_n$—COOH, wherein each $R^3$ and $R^4$ independently is a member selected from hydrogen, a substituted $C_{1-10}$ alkyl group, an unsubstituted $C_{1-10}$ alkyl group. The symbol n represents an integer from 1 to 5. The symbol $R^2$ represents a member selected from hydrogen, a substituted $C_{1-20}$ alkyl group, an unsubstituted $C_{1-20}$ alkyl group, and a group represented by the formula —(CH$_2$)$_m$CH(OH)(CH$_2$)$_p$OR$^5$, wherein m and p are independently 1 or 2, and $R^5$ is a $C_{2-20}$ acyl group, or a group represented by Formula II:

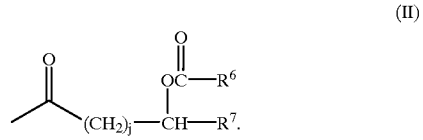

In Formula II, j is an integer from 1 to 5. The symbols $R^6$ and $R^7$ are independently selected from the group of hydrogen, a substituted $C_{1-20}$ alkyl group, and an unsubstituted $C_{1-20}$ alkyl group; or a pharmacologically acceptable salt thereof.

In a preferred embodiment, $R^2$ is a substituted or unsubstituted alkyl group having from 1 to 10 carbon atoms, more preferably from 1 to 5 carbon atoms.

In another preferred embodiment, $R^2$ is a group represented by the formula: —(CH$_2$)$_m$CH(OH)(CH$_2$)$_p$OR$^5$, in which m and p are independently 1 or 2. The symbol $R^5$ is preferably an acyl group having from 2 to 10 carbon atoms, preferably from 10 to 20 carbon atoms.

In another preferred embodiment, $R^5$ is a group represented by Formula (II) wherein j is 1, 2, or 3. $R^6$ and $R^7$ are independently selected from the group of hydrogen, a substituted $C_{1-20}$ alkyl group, and an unsubstituted $C_{1-20}$ alkyl group.

Although $R^6$ and $R^7$ can be a branched-, or straight chain, saturated or unsaturated alkyl of substantially any length, in a preferred embodiment, $R^6$ and $R^7$ are each independently alkyl groups having from 1 to 10 carbon atoms. In a further preferred embodiment, $R^6$ and $R^7$ are each independently alkyl groups having from 10 to 20 carbon atoms. In a particularly preferred embodiment, at least one of $R^6$ or $R^7$ is a substituted $C_{1-11}$ alkyl group, or an unsubstituted $C_{1-11}$ alkyl group. In addition to the compounds provided above, the present invention includes pharmacologically acceptable salts of the compounds according to Formula I.

For those embodiments in which $R^1$ is a saccharyl group, a variety of mono-, di-, or polysaccharides are useful. In one preferred embodiment, the saccharyl group is derived from the monosaccharide glucuronic acid, and is selected from either the α- or β-forms of this saccharyl group. As shown below, the site of attachment of the saccharyl group to the remainder of the molecule can be at the reducing end (i.e., the C1 position) of the saccharyl group, as is indicated by the wavy line.

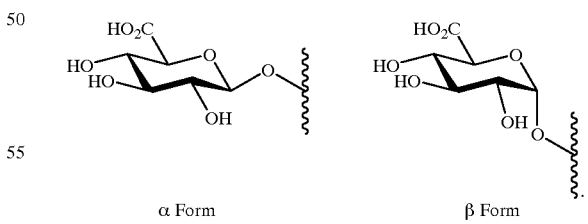

α Form      β Form

In some embodiments, it is preferred that the saccharyl group is a $C_{6-50}$ saccharyl group, more preferably a $C_{6-30}$ saccharyl group, and still more preferably a $C_{6-20}$ saccharyl group, and yet still more preferably a $C_{6-10}$ saccharyl group.

Within the above general description, a number of embodiments are particularly preferred. In one preferred embodiment, R, $R^1$ and $R^2$ are all hydrogens, and the compound is isotucaresol, represented by Formula (III):

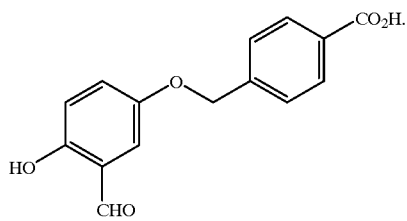

(III)

In another preferred embodiment, R is hydrogen, $R^1$ is a β-D-glucuronic acid group, $R^2$ is hydrogen, and the compound is represented by Formula (IV):

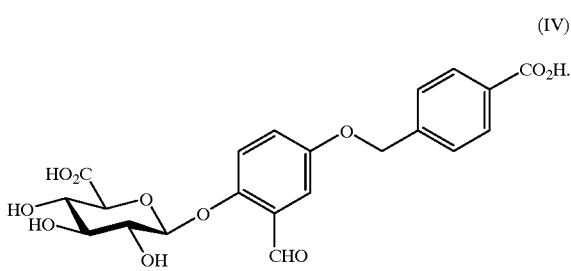

(IV)

In one embodiment, R is hydrogen, $R^1$ is a succinoyl group (i.e., $R^1$=—C(O)—[C($R^3$)($R^4$)]$_n$—COOH, wherein $R^3$ and $R^4$ are hydrogen; n is 2 and $R^2$ is hydrogen. The compound is represented by Formula (V):

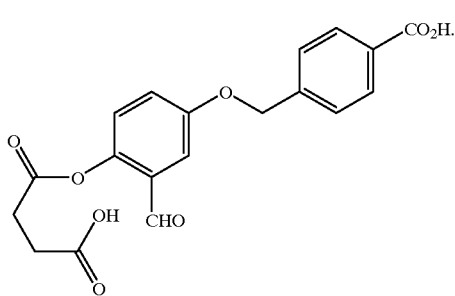

(V)

In one embodiment, R is hydrogen, $R^1$ is a β-D-glucuronic acid group, and $R^2$ is an 1-O-acyl-sn-glyceryl group (sn=stereospecifically numbered; see, Carb. Res. 1998, 312, 167), and the compound is represented by Formula (VI):

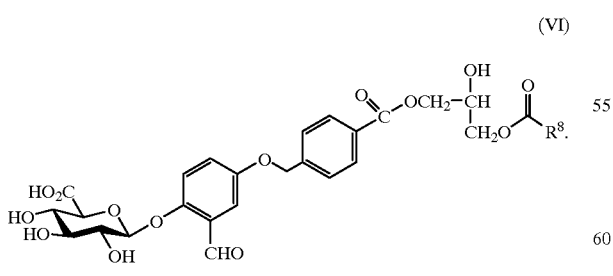

(VI)

In one embodiment, the acyl group of the 1-O-acyl-sn-glyceryl moiety is acetyl (e.g., $R^8$ in Formula VI is methyl; compound 6a), and in another embodiment, octanoyl ($R^8$ is heptyl; compound 6b), and in one embodiment, tetradecanoyl ($R^8$ is tridecyl; compound 6c).

In another aspect, the present invention provides a compound represented by the Formula I(a):

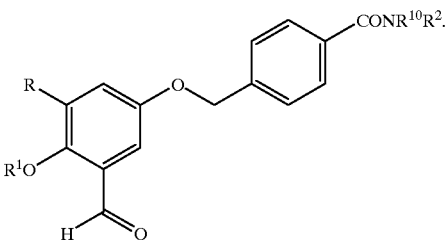

$R^2$ and $R^{10}$ are independently selected and the symbol $R^{10}$ represents a member as described above for $R^2$. Compounds of Formula I(a) are useful as adjuvants and immunoeffectors as described herein for compounds of Formula I.

In another aspect, the present invention provides a compound represented by the Formula I(b):

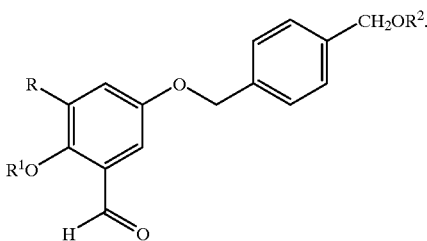

Compounds of Formula I(a) are useful as adjuvants and immunoeffectors as described herein for compounds of Formula I.

The amphipathic aldehydes according to Formulae IV–VI as saponin mimetics possess isotucaresol (Formula III) as an open-chain analog of quillaic acid (1) which is substituted with lipophilic and/or hydrophilic domains. The design of isotucaresol (Formula III) as a pharmacophore of 1 is based on the premise that saponins are more structurally complex than is necessary for optimal adjuvant effects. Similar to the steroids, the ABC-ring junctures of quillaic acid are all-trans, making the molecule relatively rigid and flat, and thus amenable to molecular mimicry by aromatic seco derivatives. Isotucaresol is an aromatic "triseco" derivative of quillaic acid in which elements of three rings (B, C, E) of the triterpene have been removed but the spatial relationship of key functionality has been maintained.

Quillaic Acid (1)

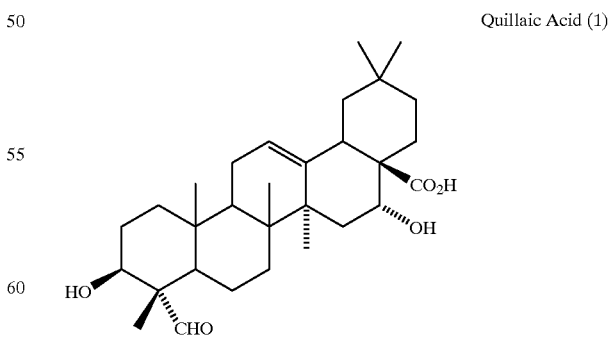

The significance of having two reactive aldehyde moieties on the A-ring of isotucaresol provides the potential for simultaneous engagement of both formyl groups in imine formation with the multiple lysyl ε-amino groups (see, Wyss et al., *Science* 1995, 269: 1273–1278) clustered in the CD2 cell-surface glycoprotein present on T lymphocytes. CD2 is believed to be the principle receptor for Schiff base-mediated costimulation of T-cells (Rhodes, 1996). Multivalent ligand-receptor interactions are common in biological systems and, in the context of T-cell activation, may help to explain not only the immunogenicity of MAA-adducted peptides but also the success of a recent cancer vaccine strategy (see, Apostolopoulos et al., *Proc. Natl. Acad. Sci., U.S.A.* 1995, 92: 10128–10132) employing formylated mucins.

By covalently bonding an antigen to an extrinsic adjuvant (immunomodulator) such as the compound of Formula I, a discrete molecule is produced which exhibits a surprisingly unexpected enhanced adjuvanting effect on the antigen which is greater than the adjuvanting effect attainable in the absence of such covalent bonding, as in a mixture of the two components (i.e., the antigen and a compound of Formula I). A further enhanced adjuvanting effect may be attained for such covalently-bonded antigen by incorporating a mineral salt adjuvant with such compounds. The mineral salt adjuvant preferably comprises aluminum hydroxide or aluminum phosphate, although other known mineral salt adjuvants, such as calcium phosphate, zinc hydroxide or calcium hydroxide, may be used.

Aqueous solubility is a desirable characteristic of adjuvant-active saponins and aids in vaccine formulation and efficacy (Kensil, 1996). Unlike oil-based emulsions and mineral salt adjuvants which can denature antigens and prevent protective effects, saponins are non-denaturing adjuvants due to their high aqueous solubility. Their high water solubility also obviates extensive homogenation procedures required for emulsion-type adjuvants, permitting simple mixing of aqueous adjuvant and antigen solutions prior to immunization. Although saponins exhibit a great deal of structural variability in the glycosides attached to C-3 and C-28 of the quillaic acid aglycon unit, the minimal carbohydrate requirement for adjuvanticity (and aqueous solubility) either alone or in formulation (with ISCOMs, alum, etc.) appears to be a glycosidically linked D-glucuronic acid (β-D—GlcA) moiety at C-3 (see, Bomford et al., *Vaccine* 1992, 10: 572–577; So et al., 1997). Thus, a D-glucuronic acid moiety, glycosidically linked to the phenol group of isotucaresol (III)—itself sparingly soluble at physiologic pH—enhances both aqueous solubility and adjuvanticity, partly by virtue of a second ionizable carboxyl group (compound (IV)). Water-soluble O-glycosides of simple hydroxybenzaldehydes (e.g., helicin (31)) not only occur in nature but readily form stable Schiff-base derivatives as well (see, *The Merck Index*, 12th ed.; Merck & Co., Inc.: Whitehouse Station, N.J., 1996) The synthetically simpler succinate (V) is also useful since succinic acid constitutes a simple 4-carbon isostere for the glucuronic acid moiety and has been used to impart triterpenes with aqueous solubility (see, Gottfried and Baxendale, U.S. Pat. No. 3,070,623, 1962).

It is important to note that chemical modification of the glucuronic carboxyl of QS-21 does not significantly alter adjuvant activity (Soltysik et al., 1995). Thus, the carboxyl group offers a unique site for attachment of a lipophilic fatty acid domain or a poorly immunogenic peptide. In fact, the attachment of simple lipophilic moieties to the glucuronic acid of deacylated Quillaja saponin or saponins lacking fatty acid domains was recently shown to enhance humoral and cell-mediated immunity (see, Marciani, WO 98/52573, 1998; and U.S Pat. No. 6,080,725). A peptide determinant linked to the glucuronic carboxyl of a compound of Formula IV (or the more lipophilic derivatives according to compounds 6a–6c) would also confer favorable solubility characteristics and potentially provide synthetic vaccines with built-in adjuvanticity. Increased immunogenicity has been observed for lipophilic Quillaja saponins covalently linked to peptide antigens via the glucuronic carboxyl (see, Kensil et al., In *Vaccines 92*; Brown, F., Chanock, R. M., Ginsberg, H. S., Lerner, R. A., Eds.; Cold Spring Harbor Laboratory Press: Plainview, N.Y., 1992; pp. 35–40).

While not wishing to be bound by the theory or rationale for using hydrophilic Schiff-base-forming compounds lacking fatty acyl groups (i.e., compounds according to Formulae IV and V as adjuvants and immunoeffectors, the use of these compounds deserves further comment. In the case of QS-21 the fatty acid domain, common also to QS-17 and QS-18, plays a critical role: controlled alkaline hydrolysis to give either a desacyl saponin (cleavage at site A in 3) or a quillaic acid derivative (cleavage at the site B) shows that neither of these two hydrolysis products nor the intact fatty acid domain enhance antibody titers or antigen-specific CTLs to ovalbumin when formulated in phosphate buffered saline (PBS) (see, Kensil et al., 1996; Kensil et al., 1992). This and other evidence suggests that antigen binding through hydrophobic interactions is reduced or eliminated when the fatty acid domain is absent. However, a recent study with the QS-21 "B fragment" isolated from unmodified crude Quillaja extract showed that this saponin (designated QS-L1, see, QS-21 partial structure) boosted humoral and cellular immune responses to recombinant hepatitis B surface antigen (rHBsAg) when administered in the presence of alum precipitated antigen. In fact, QS-L1 induced a greater total IgG response in mice than QS-21 to alum-precipitated HBsAg (So et al., 1997). These results suggest the importance of charge interaction between alum, anionic adjuvants, and peptide antigens.

The importance of the fatty acid domain to saponin adjuvanticity is further obscured by the recent structure elucidation of the hydrophilic saponin QS-7 (Kensil et al., 1998). QS-7 is a bisdesmosidic saponin possessing branched sugar units at C-3 and C-28 of quillaic acid similar to those of QS-21, but in contrast possesses an acetyl group in lieu of a large lipid domain on the fucose ring. Like QS-21, QS-7 is a potent inducer of cell-mediated and humoral responses to a variety of antigens, but lacks the characteristic hemolytic activity of saponins towards red blood cells (Kensil, 1996; Kensil et al., 1998). Hemolytic activity—thought to be due to the ability of saponin to intercalate into cell membranes and form a hexagonal array of pores involving cholesterol-complexed saponin molecules—does not correlate with adjuvant activity, however: QS-7 is non-hemolytic whereas digitonin, an adjuvant-inactive steroidal saponin, is highly hemolytic (Kensil, 1996; Kensil et al., 1998; see, Kensil et al., *J. Immunol.* 1991, 146: 431–437). Thus, CTL induction by exogenous soluble antigen does not appear to be closely associated with either saponin-induced pore formation or the presence of a complex lipophilic domain.

In addition to contributing to the greater toxicity of QS-21 and other lipophilic saponins, the complex fatty acid domain comprising two 3,5-dihydroxy-6-methyl-octanoic acid (DHMO) residues imparts considerable instability to lipophilic saponins. For example, a rapid reversible migration of the DHMO domain occurs between the 3- and 4-hydroxyl groups of fucose in QS-21, confounding purification and purity analysis as well as structure/function assessment (see, Cleland et al., *J. Pharm. Sci.* 1996, 85: 22–28).

This intramolecular transesterification can be ascribed to the known lability of β-hydroxy esters (see, Sadekov et al., *Russ. Chem. Rev.* (Eng. Transl.) 1970, 39: 179–195) (to nucleophilic attack by a vicinal hydroxyl in 3, for example).

For the same reason, base-catalyzed deacylation is a significant degradation process for QS-21 in aqueous solution, thus limiting the formulations and storage conditions with which QS-21 can be used (Kensil et al., 1995; Cleland, 1996).

Accordingly, the lipophilic derivatives (compounds 6a–c) wherein an sn-glycerol unit (same C-2 relative stereochemistry as D-fucose) has been selected as an open-chain analog of the fucose ring and simple fatty acid residues as stable substitutes for the complex DHMO residues of QS-21; acetate (compound 6a) is an analog of the more hydrophilic and less toxic QS-7. The structural relationship between compounds according to compound 6a and QS-21 is shown in bold in 3.

The synthesis of compounds according to Formulae IV–VI requires an efficient route to the isotucaresol backbone which is amenable to both scale-up and analog preparation. The original approach to a compound of Formula III, based on Kneen's multi-step synthesis of tucaresol, (see, Kneen, EP054924, 1986; and U.S. Pat. No. 4,535,183) involved benzofuran starting materials and an ozonolysis step. Other alternate routes for synthesis exist, as discussed below.

Synthesis of Compounds

From a retrosynthetic perspective (Scheme I) the lipophilic isotucaresol compounds can be divided into three major subunits: a glucuronic acid saccharyl unit, an isotucaresol nucleus, and a 3-O-acylated-sn-glycerol unit. Since compounds according Formula IV and compounds 6a–c have the glucuronic acid moiety in common, a logical way to assemble these three subunits is by initial glycosylation (or succinoylation in the case of compounds according to Formula V) of isotucaresol t-butyl ester 7 to give 8, and subsequent selective acylation of the primary hydroxyl group of advanced intermediate 9. This approach reduces the overall number of steps needed to prepare compounds of Formulae IV to VI as compared to a divergent strategy involving initial side-chain introduction (compound 6a–c) and permits the potential application of advanced intermediate 9 to the synthesis of other lipophilic derivatives. Further, this route allows incorporation of the chiral synthon 10 late in the synthesis. This synthetic strategy is also suitable for conjugating a peptide to the glucuronic carboxyl with or without a lipophilic side-chain present.

A strategy such as that outlined in Scheme I preferably utilizes orthogonal protection of the aromatic and sugar carboxyl groups as well as protection of the sugar hydroxyl groups of 8 prior to t-butyl ester deprotection and esterification with 10. A t-butyl ester is preferred for benzoate protection due to its stability to the basic conditions of certain o-formylation methods (i.e., 12→7) and its facile acidic cleavage in the presence of the allyl-based protecting groups of the glucuronide. The allyloxycarbonyl (AOC) group is readily introduced into sugars and can be removed along with the allyl ester group under neutral conditions with a palladium (O) catalyst (see, Harada et al., *J. Carbohydr. Chem.* 1995, 14, 165–170; see, Guibe, *Tetrahedron* 1998, 54: 2967–3042). Since the Mitsunobu reaction has been used for the stereoselective synthesis of aryl (see, Roush and Lin, *J. Am. Chem. Soc.* 1995, 117: 2236–2250) and other (see, Smith et al., *Tetrahedron Lett.* 1986, 27: 5813) β-glycosides from a variety of phenols and sugars including allyl glucuronate 11, (see, Juteau et al., *Tetrahedron Lett.* 1997, 38: 1481–1484) compound 8 (R═H) can be constructed directly from 7 and 11 using the Mitsunobu protocol. The isotucaresol ring system 7 can also be derived from hydroquinone (13) via benzylation with 14 and o-formylation, or alternatively via a route analogous to Kneen's tucaresol synthesis 22 from benzofuran derivatives 15 and 16.

An alternate approach to the construction of an isotucaresol linchpin, which allows ready access to either (IV)–(VI) via a route analogous to Scheme I or (compounds 6a–c) via a divergent path, o-metalation strategies (see, infra) are also useful for introducing the formyl group. Starting materials which already include an o-formyl group are also useful to prepare compounds of the invention.

Scheme I
Retrosynthesis

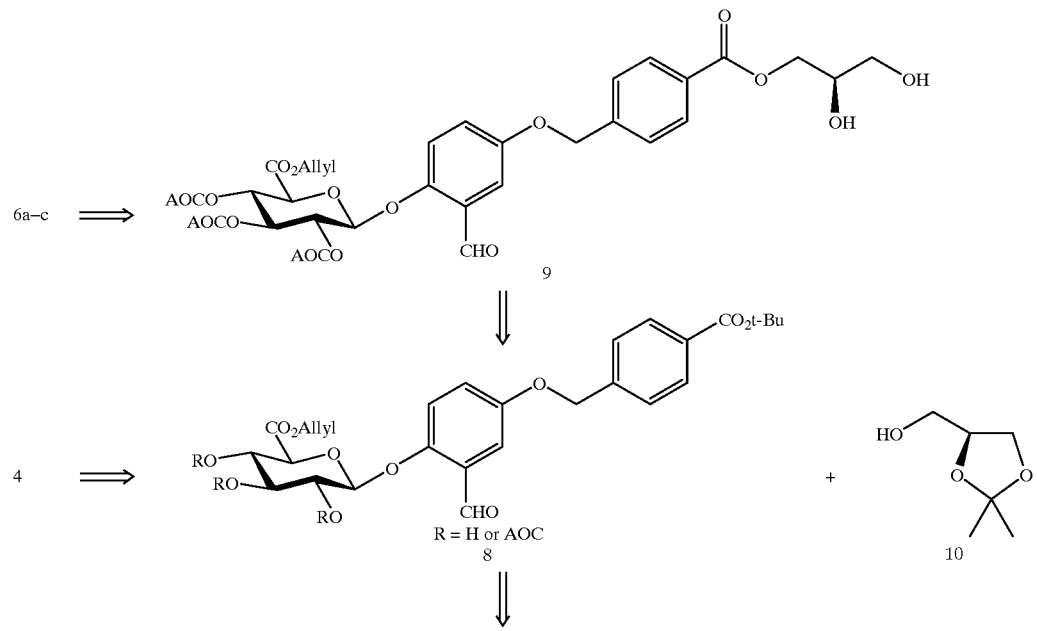

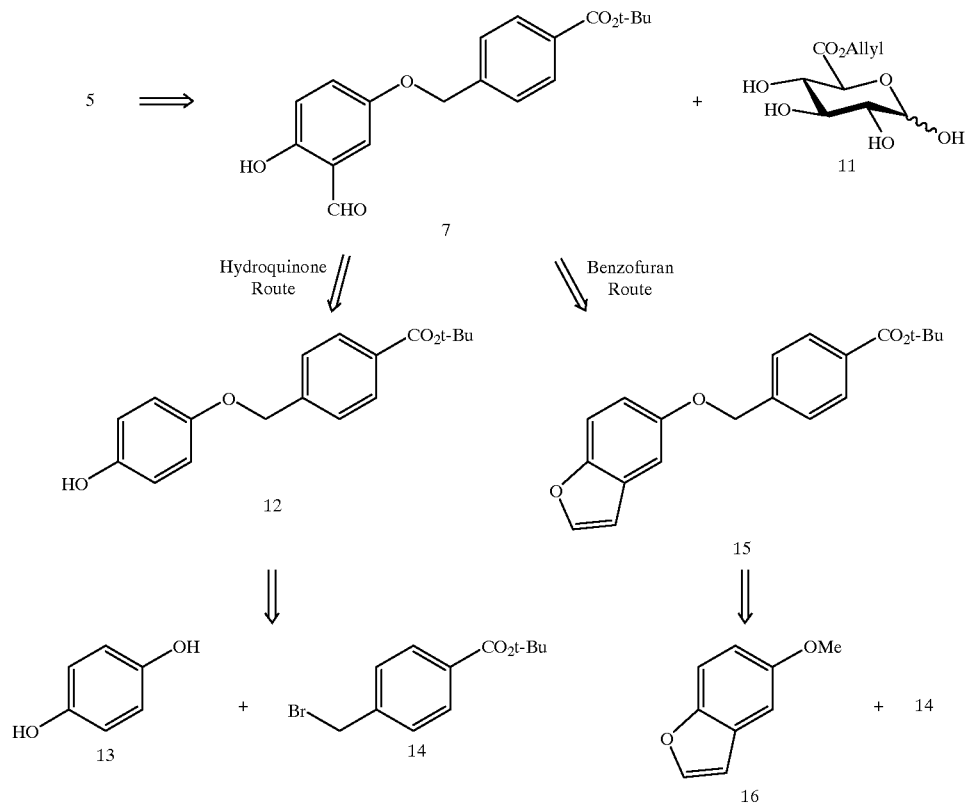

AOC = -CO₂Allyl

Synthesis of Isotucaresol t-Butyl Ester (7) Hydroquinone Route

A number of routes are available for constructing t-butyl ester 7, including the o-formylation of phenol 12 (Scheme II). The synthesis of 12 can be readily achieved by monobenzylation of hydroquinone (13) with bromide 14 in the presence of potassium carbonate (see, Schmidhammer and Brossi, *J. Org. Chem.* 1983, 48: 1469–1471) in $CHCl_3$—MeOH or MeOH or via a recently reported monobenzylating method (see, Zacharie et al., *J. Chem. Soc., Perkin Trans. 1* 1997, 19: 2925–2930) using $Cs_2CO_3$ in dimethylformamide (DMF) (The monobenzylation of hydroquinone can also be achieved with free acid 17 under standard conditions ($K_2CO_3$/MeOH, rt; 60%)). The known t-butyl ester 14 can be prepared according to Zacharie's method (see, Zacharie et al., *J. Org. Chem.* 1995, 60: 7072–7074) from commercially available 17 with 2-ethoxy-1-ethoxycarbonyl-1,2-dihydroquinoline (EEDQ) and t-BuOH or via one of the other common methods for t-butyl ester formation, such as dicyclohexylcarbodiimide/dimethylaminopyridine (DCC/DMAP) esterification (see, Neises and Steglich, *Org. Synth.* 1984, 63: 183–187; Greene and Wuts (1991) *Protective Groups in Organic Synthesis*, 2nd edition, John Wiley & Sons, Inc).

The Reimer-Tiemann reaction can also be used to o-formylate phenols bearing p-substituents (see, Jung and Lazarova, *J. Org. Chem.* 1997, 62: 1553–1555 and references cited therein.) Thus, treatment of 12 with solid sodium hydroxide and 2 equivalents of water in chloroform at reflux provides isotucaresol t-butyl ester 7 directly.

Scheme II

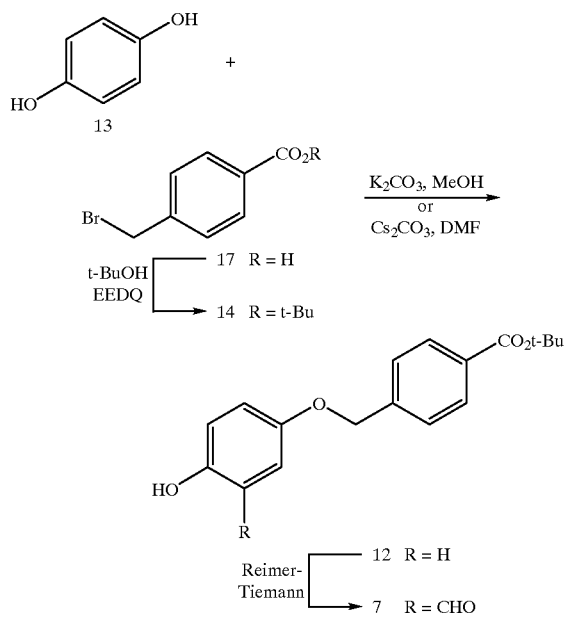

A second method is also available for introducing an o-formyl group into phenol 12 (Scheme III). Recently, Yamaguchi (see, Yamaguchi et al., *J. Org. Chem.* 1998, 63: 7298–7305) reported that functionalized phenols can be efficiently vinylated at the ortho position with acetylene in the presence of SnCl$_4$—Bu$_3$N reagent. Since aryl olefinic groups can be oxidatively cleaved to benzaldehydes in high yield with a variety of reagents (e.g., OsO$_4$/NaIO$_4$, RuO$_2$/NaIO$_4$) (see, Singh and Samanta, *B. Synth. Commun.* 1997, 27: 4235–4244; see, Hudlicky, M. *Oxidations in Organic Chemistry;* Monograph Series 186; American Chemical Society: Washington, D.C., 1990; pp. 77–81)—even in the presence of a free phenolic hydroxyl group, (Singh and Samanta, 1997) the phenol 12 can be converted to salicaldehyde derivative 7 via a two-step process involving stannylacetylene-mediated vinylation of 12 to give 18 and subsequent oxidation with OsO$_4$/NaIO4 in aq. dioxane. Alternatively, the crude 18 can be acetylated during work-up—a tactic known to improve vinylphenol stability—and deacetylated (K$_2$CO$_3$/MeOH, rt) following oxidation.

Scheme III

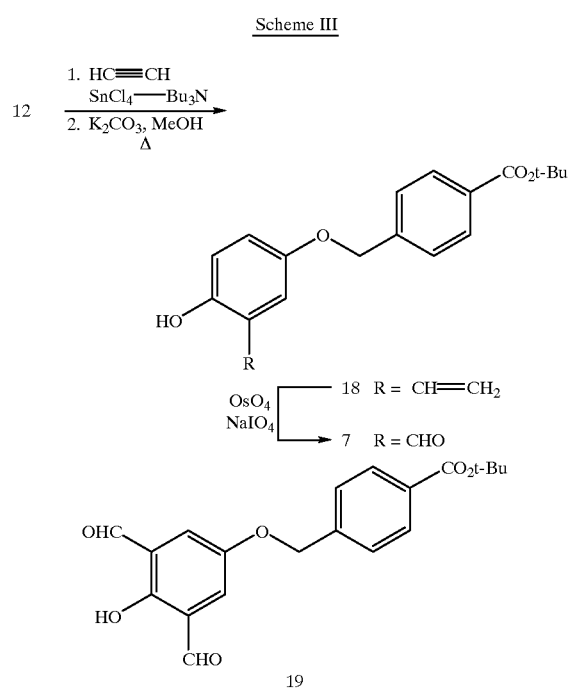

The o-vinylation reaction with acetylene should also allow ready access to the corresponding dicarboxaldehyde 19 and related diformyl derivatives of this invention via divinylation/oxidation of 12 using Yamaguchi's modified reaction conditions for preparing 2,6-divinyl phenols (Yamaguchi et al., 1998). The adjuvant activity of 19 and substituted derivatives can be evaluated using methods described herein.

Directed Metalation Approach to 7

An alternate approach to the o-hydroxybenzaldehyde portion of 7 is the o-metalation of methoxymethyl (MOM)-protected phenol 20 (Scheme IV). The powerful ortho directing ability of the MOM group, coupled with its facile acidic cleavage and base stability, make MOM-ethers especially useful for functionalizing aromatic compounds (see, Zacharie et al., 1997; see, Ronald and Winkle, *Tetrahedron* 1983, 39: 2031–2042). Thus, hydroquinone 13 can be selectively monoprotected (Zacharie et al., 1997; see, Cruz-Almanza et al., *Heterocycles* 1994, 37: 759–774) with chloromethyl methyl ether in acetone in the presence of Cs$_2$CO$_3$ or via the phenoxide generated with NaH in tetrahydrofuran (THF) to give the known (Cruz-Almanza et al., 1994) MOM-protected phenol 21. Benzylation of 21 with acid 17 in the presence of K$_2$CO$_3$ then yields 20. Treatment of 20 with two equivalents of n- or s-butyllithium (RLi) in THF at −78° C. with or without added tetramethylethylenediamine generates the dilithio species, which on quenching at low temperature with DMF yields MOM-protected isotucaresol 22 after aq. NH$_4$Cl work-up. Directed metalations in the presence of a carboxyl group at low temperature occur without nucleophilic attack (by RLi) on the carboxylate (see, Johnson and Gribble, *Tetrahedron Lett.* 1987, 28: 5259–5262). It is also possible to convert hydroxy acid 23 directly to 22 by tandem MOM-protection-directed metalation reaction according to the protocol shown in Scheme IV. Similarly, selective methoxymethylation of the dilithio salt of 23 provides an alternate preparation of MOM-ether 20.

Scheme IV

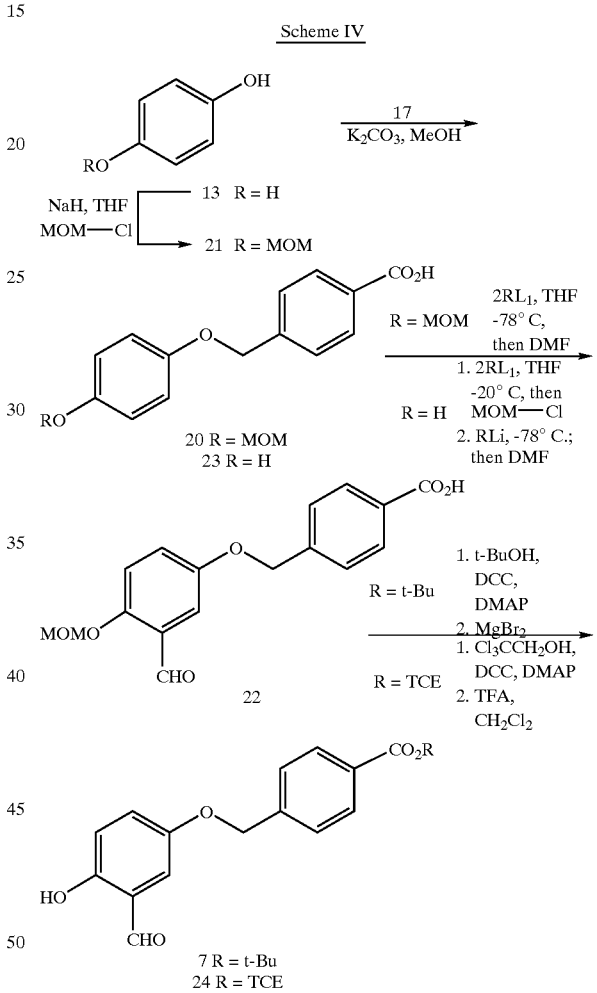

Because compounds 7 and 22 are diametrically protected, 22 is preferred for attaching the lipophilic side-chain first. A compound comprising both lipophilic and hydrophilic domains can be constructed from 22 in as few as 6 steps this way—potentially an important consideration with respect to the large-scale chemical synthesis of an adjuvant candidate.

Compound 22 permits protection of the carboxylic function with groups other than t-butyl since base stability (to phenol o-formylation) is obviated. Selective deprotection of the MOM group in the presence of a t-butyl ester is possible with reagents such as B-bromocatecholborane or MgBr$_2$, where removal is facilitated by chelation with the neighboring carbonyl (see, Haraldsson and Baldwin, *Tetrahedron.* 1997, 53: 215–224). Alternatively, initial deprotection of the MOM group and selective t-butyl ester formation using in situ-generated isobutylene (see, Wright et al., *Tetrahedron Lett.* 1997, 38: 7345–7348) can be used to provide intermediate 7. Accordingly, 22 is converted to 7 by one these two protocols or, alternatively, to the 2,2,2-trichloroethyl (TCE) ester 24 by carbodiimide esterification and MOM removal with TFA, etc. TCE esters are stable to a greater range of glycosylating conditions than t-butyl esters, but like t-butyl groups are orthogonal to allyl-based sugar protection (see, Greene and Wuts, *Protective Groups in Organic Synthesis;* 2nd ed.: John Wiley & Sons, Inc.: New York, 1991; pp. 240–241).

Synthesis of 7 from 2,5-Dihydroxybenzaldehyde (25)

One variation on the hydroquinone strategy, which—like the benzofuran route below—commences with a fully functionalized A-ring, is the selective benzylation of 2,5-dihydroxybenzaldehyde (25) on the more nucleophilic 5-hydroxyl group. Thus, treatment of commercially available 25 with bromide 14 under conditions known to selectively alkylate the hydroxyl meta to the carbonyl group in 2,5-dihydroxy systems (see, Sadekov et al., 1970; see, Vyas and Shah, *Org. Synth.,* Coll. Vol. 4 1963, pp. 836–839) can be used to provide intermediate 7 in just two steps (Scheme V). Likewise, alkylation of 25 with acid 17 gives isotucaresol (III) in a single step.

Scheme V

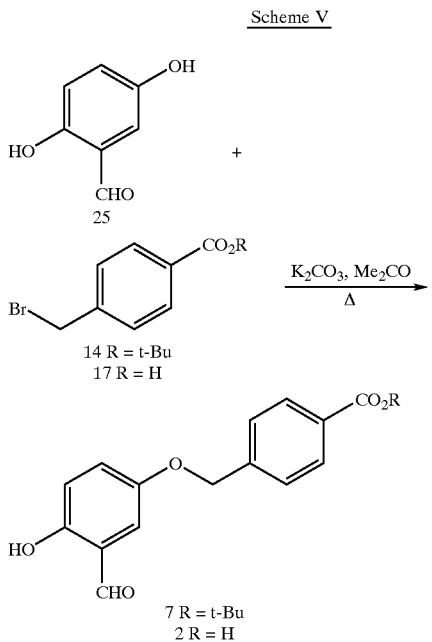

Selective Debenzylation Ortho to an Aromatic Carbonyl Group to Yield 7 or (III)

Compounds according to the formulae of 7 or III can be made by selective debenzylation. For example, a dibenzylated product formed as a side product in the preparation of 7 (or III) in Scheme V can be selectively cleaved at the site ortho to the formyl group with $MgBr_2$ (see, Haraldsson and Baldwin, 1997). Alternatively, quantitative dibenzylation of 25 with 14 or 17, or other appropriate derivatives followed by selective o-debenzylation also provides an efficient route to (III) and its derivatives (e.g., compound 40). The simplicity of these methods offsets the greater expense of the starting material 25 as compared to hydroquinone 13.

Generally, this reaction scheme is carried out on in the presence of a Lewis acid to form the selectively debenzylated product as in Scheme VI:

Scheme VI

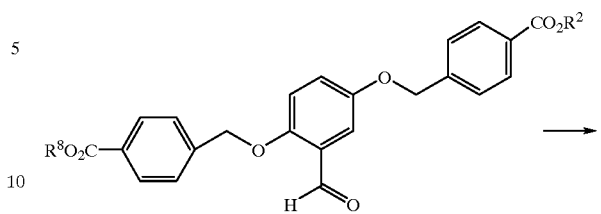

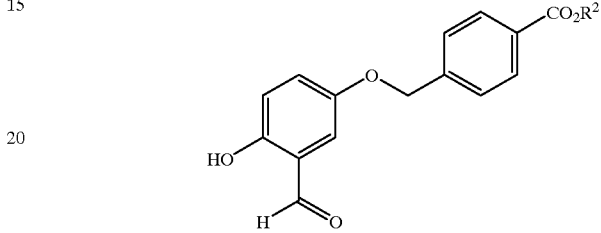

$R^2$ and $R^8$ can be the same or different. In some embodiments, $R^2$ and $R^8$ are selected from moieties which are known in the art as carboxylic acid protecting groups. Compounds within the scope of the invention include embodiments where $R^2$ and $R^8$ are independently selected from hydrogen, a substituted $C_{1-20}$ alkyl group, an substituted $C_{1-20}$ alkyl group, and a group having the formula $-(CH_2)_m CH(OH)(CH_2)_p OR^5$, wherein m and p are independently 1 or 2, and $R^5$ is a substituted $C_{2-20}$ acyl group, an substituted $C_{2-20}$ acyl group, or a group having the formula:

The symbol j represents an integer from 1 to 5. The substituents $R^6$ and $R^7$ can independently represent hydrogen, a substituted $C_{1-20}$ alkyl group, or an substituted $C_{1-20}$ alkyl group.

The o-debenzylation can be achieved with a Lewis acid having the formula $MX_n$. M is selected from the group containing $Al^{3+}$, $As^{3+}$, $B^{3+}$, $Fe^{2+}$, $Fe^{3+}$, $Ga^{3+}$, $Mg^{2+}$, $Sb^{3+}$, $Sb^{5+}$, $Sn^{2+}$, $Sn^{4+}$, $Ti^{2+}$, $Ti^{3+}$, $Ti^{4+}$, and $Zn^{2+}$. X is a halide delected from the group consisting of Cl, I, F, and Br. Those of skill in the art will recognize that n is an integer from 2 to 5 depending on the valence state of M. In some embodiments, the Lewis acids that can be used to achieve the ortho-debenzylation include, but are not limited to: $AlCl_3$, $AlI_3$, $AlF_3$, $AlBr_3$, $Et_2AlCl$, $EtAlCl_2$, $AsCl_3$, $AsI_3$, $AsF_3$, $AsBr_3$, $BCl_3$, $BBr_3$, $BI_3$, $BF_3$, $BCl_3.SMe_2$, $BI_3.SMe_2$, $BF_3.SMe_2$, $BBr_3.SMe_2$, $FeCl_3$, $FeBr_3$, $FeI_3$, $FeF_3$, $FeCl_2$, $FeBr_2$, $FeI_2$, $FeF_2$, $GaCl_3$, $GaI_3$, $GaF_3$, $GaBr_3$, $MgCl_2$, $MgI_2$, $MgF_2$, $MgBr_2$, $MgCl_2$—$OEt_2$, $MgI_2$—$OEt_2$ $MgF_2$—$OEt_2$ $MgBr_2$—$OEt_2$, $SbCl_3$, $SbI_3$, $SbF_3$, $SbBr_3$, $SbCl_5$, $SbI_5$, $SbF_5$, $SbBr_5$, $SnCl_2$, $SnI_2$, $SnF_2$, $SnBr_2$, $SnCl_4$, $SnI_4$, $SnF_4$, $SnBr_4$, $TiBr_4$, $TiCl_2$, $TiCl_3$, $TiCl_4$, $TiF_3$, $TiF_4$, $TiI_4$, $ZnCl_2$, $ZnI_2$, $ZnF_2$, and $ZnBr_2$. In addition, the o-debenzylation can be achieved with Lewis acids such as $Et_2AlCl$, $EtAlCl_2$, monoalkyl boronhalides, dialkyl boronhalides, and monoaryl boronhalides, diaryl boronhalides. X can be, but is not limited to, Cl, I, F, and Br. The reaction is carried out under conditions sufficient to form the ortho-debenzylated product. These conditions can be determined by one of skill in the art by optimizing reaction parameters. Reaction parameters that can be optimized in the ortho-debenzylation reaction include, but are not limited to, length of reaction incubation, temperature, pressure, solvent(s), ratio of solvent to starting materials, etc. Methods of optimizing reactions of the present invention are well within the purview of one skilled in the organic chemistry arts.

Without being bound by any particular theory, the reaction of these Lewis Acids with the dibenzylated starting material is thought to form a multi-membered (e.g., six-membered) chelation ring intermediate. This multi-membered chelation ring intermediate is then subjected to hydrolysis (e.g., with a base, an acid, HCl, etc.) to yield the ortho-debenzylated product. The addition of a base or acid to the reaction mixture can be considered part of the conditions sufficient to form the desired ortho-debenzylated product.

In some embodiments, the o-debenzylation is carried out by reacting compound 39 under condition A, condition B, or condition C to give methyl 4-(3-formyl-4-hydroxyphenoxymethyl)benzoate (isotucaresol methyl ester; 40):

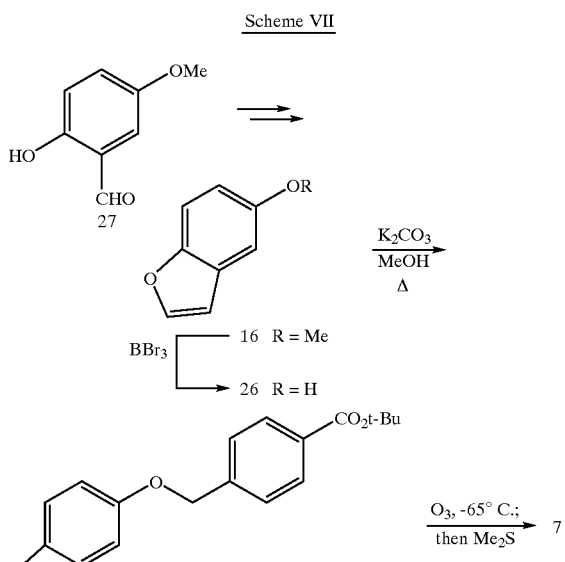

Scheme VII

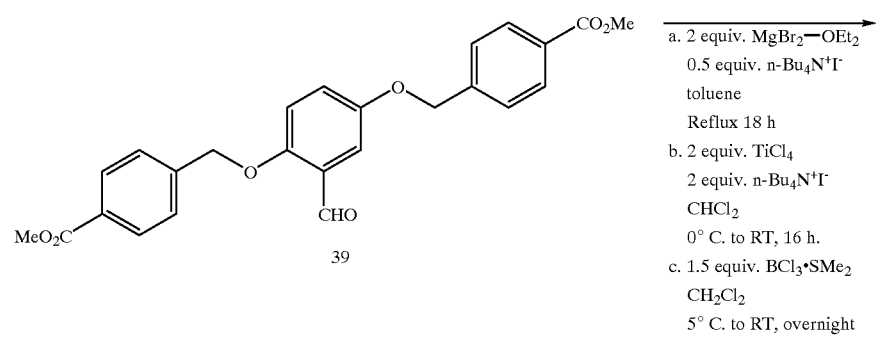

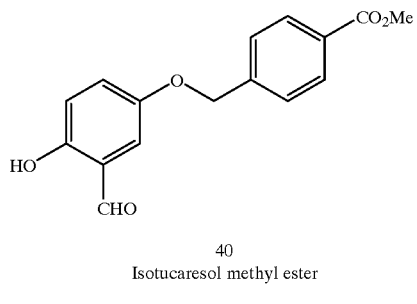

40
Isotucaresol methyl ester

Benzofuran Route

In one synthesis of isotucaresol (III), commercially available 5-methoxybenzofuran (16) is demethylated with boron tribromide (see, Williard and Fryhle, *Tetrahedron Lett.* 1980, 21: 3731–3734) to give 26, which is then benzylated with methyl 4-(bromomethyl)benzoate. Analogous benzylation of 26 with t-butyl ester 14 and ozonolysis (Kneen, EP054924, 1986; and U.S. Pat. No. 4,535,183) of benzofuran intermediate 15 provides compound 7 (Scheme VII).

Synthesis of Hemisuccinate (V)

Conversion of phenols and alcohols to their corresponding hemisuccinates (isolated as the free acid or alkali metal salt) is a common tactic to enhance aqueous solubility of steroids and other lipophilic drugs, and consequently general methods are available for succinoylation (see, Gottfried and Baxendale, 1962). Treatment of t-butyl ester 7 with succinic anhydride in pyridine yields compound (V) subsequent to deprotection of the t-butyl ester with trifluoroacetic acid (TFA) (Scheme VIII). Since quaternary carboxylic acid groups do not ordinarily interfere with this reaction, the direct succinoylation of isotucaresol (III) is also possible.

Scheme VIII

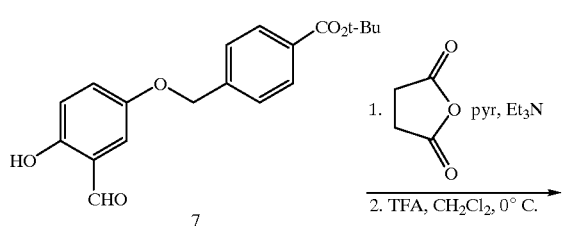

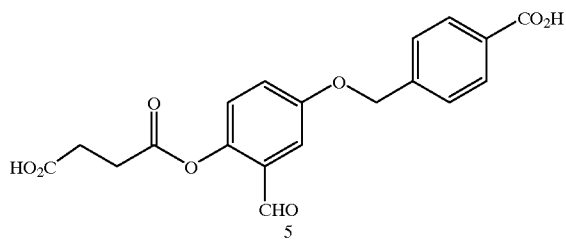

Synthesis of Glucuronide 4

The highly stereoselective synthesis of aryl β-glycosides and acyl β-glucuronides has been achieved via the Mitsunobu reaction (see, Roush and Lin, 1995; see, Smith et al., 1986). In fact, allyl glucuronate 11 has been used in the Mitsunobu reaction without protection of sugar hydroxyl groups in yields up to 50% by taking advantage of the higher reactivity of the anomeric hydroxyl group (see, Juteau et al., 1997). Application of the Mitsunobu protocol to fully protected sugars gives even higher yields (70–95%) of aryl β-glycosides (see, Roush and Lin, 1995).

Accordingly, the known (Juteau et al., 1997) allyl ester 11, prepared from D-glucuronic acid and allyl bromide (1,8-diazobicyclo[5.4.0]undec-7-ene (DBU)/DMF, rt) in 75% yield, is selectively coupled with phenol 7 or a related derivative in the presence of triphenylphosphine and diisopropylazodicarboxylate (DIAD) in THF at 0° C. to give aryl β-glycoside 28 (i.e., 8 R=H) as shown in Scheme IX. Sequential deprotection of the ester protecting groups with TFA and Pd(0) in the presence of a suitable allyl scavenger (see, Harada et al., 1995; see, Guibe, 1998) then gives compound (IV).

Scheme IX

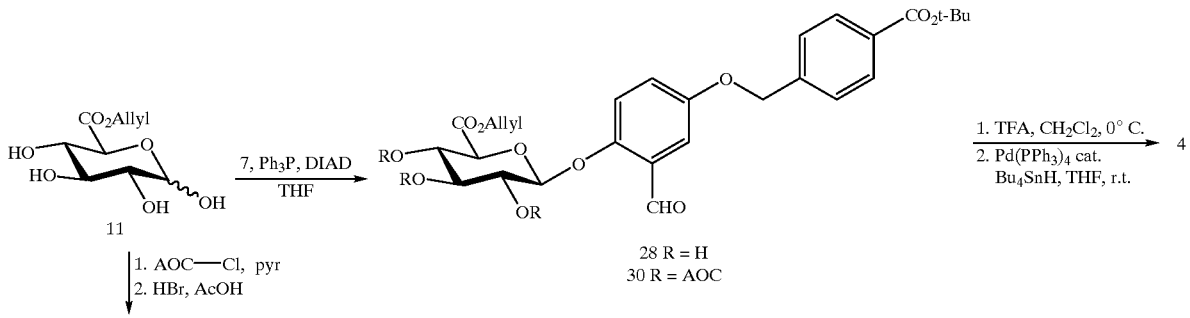

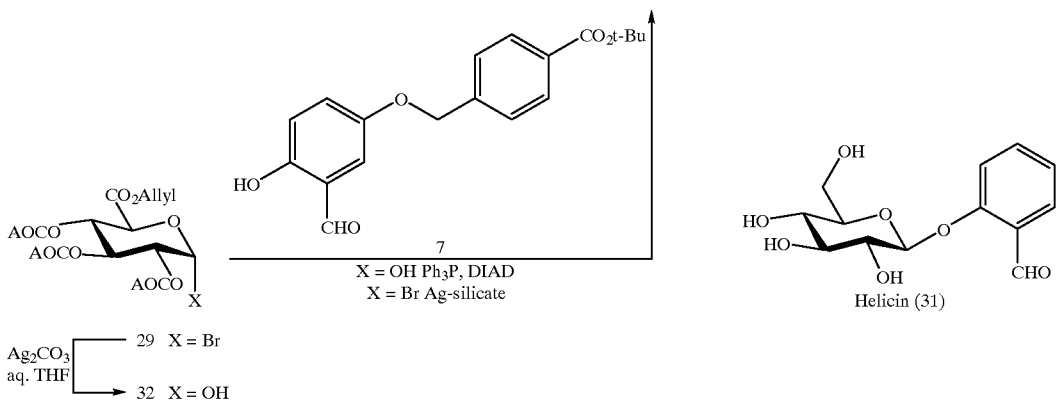

An alternate method which has been used for the glycosylation of phenols is the Koenigs Knorr reaction of pyranosyl bromides in the presence of a silver salt (see, Roush and Lin, 1995; see, Robertson and Waters, R. B. J. Chem. Soc. 1930, 2729–2733) Since AOC groups have been introduced onto the 2,3,4-positions of glucuronides in high yield using AOC-Cl in pyridine, (see, Harada et al., 1995) 11 is similarly protected and then treated with HBr in acetic acid to give bromide 29. Silver mediated coupling of 29 and 7 then gives predominantly the aryl β-glycoside 30 (i.e., 8, R=AOC). An analogous glycosylation has been used to prepare the natural product helicin (31) from salicaldehyde and O-tetraacetyl-4-D-glucopyranosyl bromide in the presence of silver oxide (see, Robertson and Waters, 1930). Glycosyl donor 29 also provides access to lactol 32 by silver-mediated hydrolysis (see, Roush and Lin, 1995). Mitsunobu reaction of fully protected 32 with 7 should also give 30, which can then be deprotected to 4 by the same 2-step deprotection as for 28.

Synthesis of Glucuronides 6a–6c

Aryl glycoside 30, prepared directly from 29 or 32 as discussed above or, alternatively, by AOC-protection of 28, is transformed into the advanced intermediate 9 by the sequence: (1) t butyl ester hydrolysis, (2) esterification with 10, and (3) acetonide cleavage as shown in Scheme X below.

is sensitive to ketal and/or t-butyl ester cleavage, TCE ester 24—prepared from 22 or via ester interchange of 7—can be used for glucuronidation and subsequently deprotected under neutral conditions with zinc in buffered aq. THF (see, Just and Grozinger, Synthesis 1976, 457–458). Stable isosteres (pseudosugar, C-glycoside) of the glucuronide can be prepared.

Compound 9 is selectively acylated on the primary hydroxyl group with acetic anhydride and the appropriate acid chlorides under standard conditions to give 33a–c. Although acetylations with acetyl chloride are not as selective as with other acid chlorides, acetyl introduction with $Ac_2O$ in $CHCl_3$ in the presence of pyridine provides good selectivity for primary alcohols when the reaction is run below 0° C. (see, Stork et al., J. Am. Chem. Soc. 1978, 100: 8272–8273). One method that has been applied specifically to the selective acylation of glycerol derivatives is the reaction of an in situ-generated stannoxane—prepared with $Bu_2SnO$ in toluene by azeotropic dehydration—with acid chlorides at 0° C. (see, Aragozzini et al., Synthesis 1989, 225–227). Deprotection of the allyl-based protecting groups of 33a–c prepared by one of these methods delivers (6a–c).

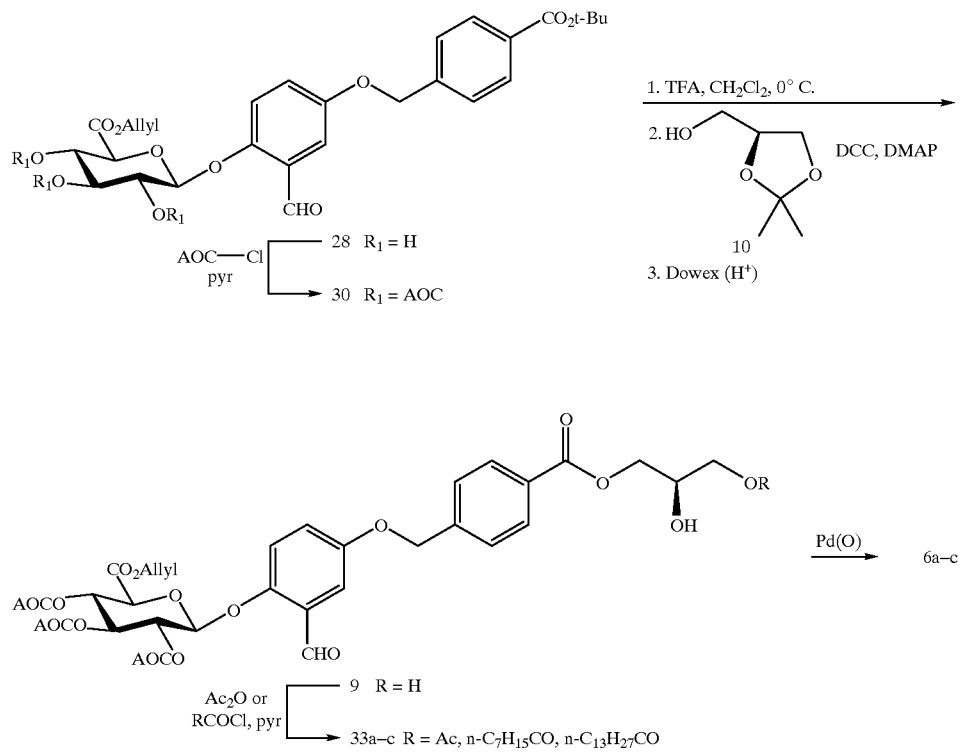

Scheme X

Recently, in an approach to aureolic acid antibiotics it was demonstrated that aryl glycosides possessing electron-withdrawing substituents on the aromatic aglycon are stable to acidic deprotection of ketal and other protecting groups (Roush and Lin, 1995; Roush et al., J. Am. Chem. Soc. 1999, 121: 1990–1991). In fact, certain phenyl glycosides bearing carbonyl groups in the aglycon unit have shown remarkable stability to acidic hydrolysis (see, Bär et al., Wiss. Technol. 1990, 23: 371–376). Nevertheless, if the glycosidic linkage Divergent Synthesis of 6a–c As discussed above, MOM ether 23 is ideally suited for elaborating the acylated glycerol unit prior to glucuronidation of the phenolic hydroxyl group. Thus, esterification of 23 with 10, followed by acetonide hydrolysis and acylation as described above should yield 34a–c (Scheme XI). MOM deprotection and Mitsunobu coupling of the resulting 35a–c with 11 then provides glucuronides 36a–c, which can be deprotected with Pd(0) to give 6a–c.

Scheme XI

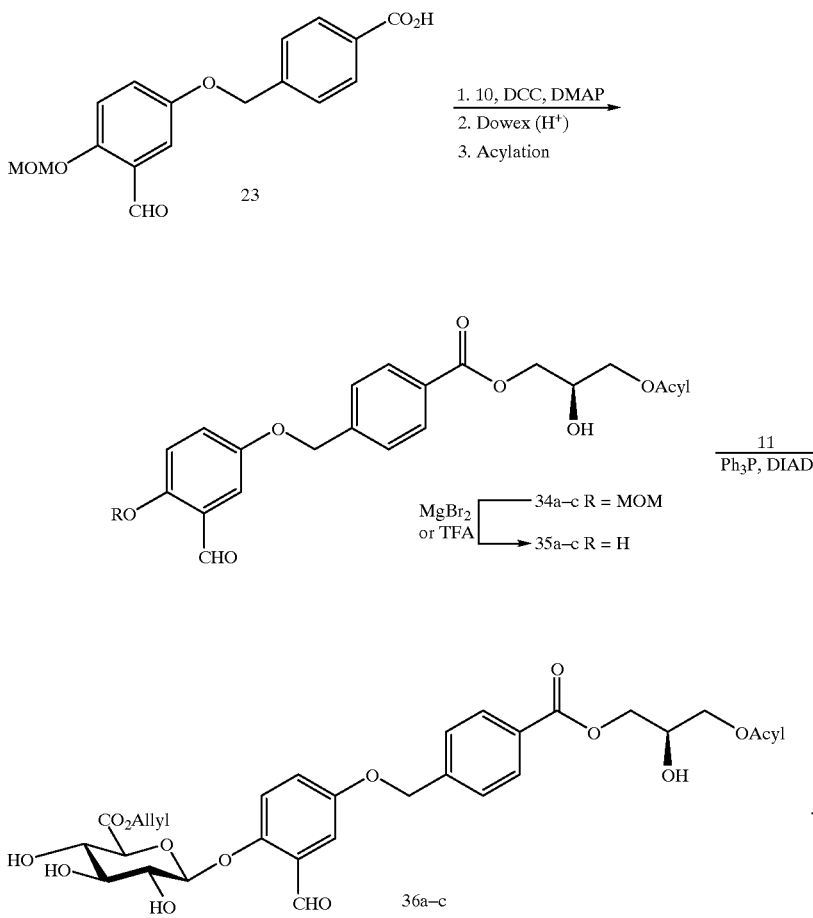

Finished products (IV–VI) are analyzed by standard spectroscopic (IR, $^1$H and $^{13}$C NMR) and physical (elemental and HRMS) data. Purity is assessed by reverse-phase HPLC analysis of the intact molecules or a suitable derivative (e.g., phenacyl ester of the glucuronic carboxyl group).

Evaluation of Compounds

The adjuvant effects of the compounds of the present invention on humoral and cell-mediated responses can be determined in two different murine models using rHBsAg (recombinant Hepatitis B Surface Antigen), inactivated influenza virus (e.g., hemagglutinin protein in FluZone influenza vaccine (Connaught Laboratories, Swiftwater, Pa.)) as antigens. In the case of rHBsAg, the compounds can be formulated with both alum-adsorbed antigen and soluble antigen and compared with an alum-adsorbed antigen control. Antibody titers (e.g., IgG, IgG1, IgG2a, IgG2b, etc.) to rHBsAg can be determined by ELISA from pre-vaccination and post-vaccination sera.

Given the enhanced serum and mucosal CTL and IgA responses often elicited with vaccines administered intranasally (i.n.), (see, VanCott et al., *J. Immunol.* 1998, 160: 2000–2012; Imaoka et al., *J. Immunol.* 1998, 161: 5952–5958) both i.n. and subcutaneous (s.c.) immunization of mice are performed with the above formulations. The compounds are evaluated for their ability to induce rHBsAg-specific antibodies and influenza hemagglutinin-specific antibodies in BALB/c mice and enhance CTLs against P815S-HBsAg target cells (see, e.g., Moore et al., (1988) *Cell* 55: 777–785). The P815S cell line is a transfectant of P815 which expresses the HBsAg $CTL_{S28-39}$ epitope in the MHC-I complex and shows relevance to human immune responses to hepatitis B virus (HBV), for which CTL responses appear to be important for pathogen clearance (see, Schirmbeck et al., *J. Immunol.* 1994, 152: 1110–1119; see, Schirmbeck et al., *J. Virol.* 1994, 68: 1418–1425).

The pyrogenicity of the compounds of the claims invention can be assayed using methods known in the art. Pyrogenicity is typically assayed by intravenous injection of a compound being tested (e.g., at a 10 μg/Kg dose) and measuring the total rise in the temperature of the animal injected (e.g., a rabbit, a mouse, etc).

Pharmaceutical Compositions and Vaccine Compositions

In one embodiment, the present invention provides pharmaceutical compositions containing a compound of the present invention and a pharmaceutically acceptable carrier. The compound is present in a therapeutically effective amount, which the amount of compound required to achieve the desired effect in terms of treating a disease, condition, or achieving a biological occurrence.

In another embodiment of the invention, the adjuvant system of the present invention can be administered without a co-administered antigen, to potentiate the immune system for treatment of chronic infectious diseases, especially in immune compromised patients. Illustrative examples of infectious diseases for which this approach may be employed for therapeutic or prophylactic treatment can be found in U.S. Pat. No. 5,508,310. Potentiation of the immune system in this way can also be useful as a preventative measure to limit the risks of nosocomial and/or post-surgery infections.

The pharmaceutical compositions can act as an adjuvant when co-administered with an antigen. The compounds of Formula I can be thought of as the extrinsic adjuvant. An adjuvant is an immunostiumulatory agent that enhance the immunogenicity of an antigen but is not necessarily immunogenic itself. Intrinsic adjuvants, such as lipopolysaccharides, normally are the components of the killed or attenuated bacteria used as vaccines. Extrinsic adjuvants are immunomodulators which are typically non-covalently linked to antigens and are formulated to enhance the host immune responses. In one embodiment, the antigen is a tumor associated antigen (tumor specific antigen).

In one embodiment the present invention provides a vaccine composition comprising an antigen and a compound of Formula I. Suitable antigens include microbial pathogens, bacteria, viruses, proteins, glycoproteins lipoproteins, peptides, glycopeptides, lipopeptides, toxoids, carbohydrates, and tumor-specific antigens. Mixtures of two or more antigens may be employed.

Thus, the adjuvant systems of the invention are particularly advantageous in making and using vaccine and other immunostimulant compositions to treat or prevent diseases, such inducing active immunity towards antigens in mammals, preferably in humans. Vaccine preparation is a well developed art and general guidance in the preparation and formulation of vaccines is readily available from any of a variety of sources. One such example is New Trends and Developments in Vaccines, edited by Voller et al., University Park Press, Baltimore, Md., U.S.A. 1978.

The vaccine compositions of the present invention may also contain other compounds, which may be biologically active or inactive. For example, one or more immunogenic portions of other tumor antigens may be present, either incorporated into a fusion polypeptide or as a separate compound, within the vaccine composition. Polypeptides may, but need not, be conjugated to other macromolecules as described, for example, within U.S. Pat. Nos. 4,372,945 and 4,474,757. Vaccine compositions may generally be used for prophylactic and therapeutic purposes.

In one illustrative embodiment, the antigen in a vaccine composition of the invention is a peptide, polypeptide, or immunogenic portion thereof. An "immunogenic portion," as used herein is a portion of a protein that is recognized (i.e., specifically bound) by a B-cell and/or T-cell surface antigen receptor. Such immunogenic portions generally comprise at least 5 amino acid residues, more preferably at least 10, and still more preferably at least 20 amino acid residues of an antigenic protein or a variant thereof.

Immunogenic portions of antigen polypeptides may generally be identified using well known techniques, such as those summarized in Paul, *Fundamental Immunology*, 3rd ed., 243–247 (Raven Press, 1993) and references cited therein. Such techniques include screening polypeptides for the ability to react with antigen-specific antibodies, antisera and/or T-cell lines or clones. As used herein, antisera and antibodies are "antigen-specific" if they specifically bind to an antigen (i.e., they react with the protein in an ELISA or other immunoassay, and do not react detectably with unrelated proteins). Such antisera and antibodies may be prepared as described herein, and using well known techniques. An immunogenic portion of a protein is a portion that reacts with such antisera and/or T-cells at a level that is not substantially less than the reactivity of the full length polypeptide (e.g., in an ELISA and/or T-cell reactivity assay). Such immunogenic portions may react within such assays at a level that is similar to or greater than the reactivity of the full length polypeptide. Such screens may generally be performed using methods well known to those of ordinary skill in the art, such as those described in Harlow and Lane, *Antibodies: A Laboratory Manual*, Cold Spring Harbor Laboratory, 1988. For example, a polypeptide may be immobilized on a solid support and contacted with patient sera to allow binding of antibodies within the sera to the immobilized polypeptide. Unbound sera may then be removed and bound antibodies detected using, for example, $^{125}$I-labeled Protein A.

Peptide and polypeptide antigens are prepared using any of a variety of well-known techniques. Recombinant polypeptides encoded by DNA sequences may be readily prepared from isolated DNA sequences using any of a variety of expression vectors known to those of ordinary skill in the art. Expression may be achieved in any appropriate host cell that has been transformed or transfected with an expression vector containing a DNA molecule that encodes a recombinant polypeptide. Suitable host cells include prokaryotes, yeast, and higher eukaryotic cells, such as mammalian cells and plant cells. Preferably, the host cells employed are *E. coli*, yeast or a mammalian cell line such as COS or CHO.

Portions and other variants of a protein antigen having less than about 100 amino acids, and generally less than about 50 amino acids, may also be generated by synthetic means, using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See, Merrifield, *J. Am. Chem. Soc.* 85:2149–2146, 1963. Equipment for automated synthesis of polypeptides is commercially available from suppliers such as Perkin Ehner/Applied BioSystems Division (Foster City, Calif.), and may be operated according to the manufacturer's instructions.

Within certain specific embodiments, a polypeptide antigen used in the vaccine compositions of the invention may be a fusion protein that comprises two or more distinct polypeptides. A fusion partner may, for example, assist in providing T helper epitopes (an immunological fusion partner), preferably T helper epitopes recognized by humans, or may assist in expressing the protein (an expression enhancer) at higher yields than the native recombinant protein. Certain preferred fusion partners are both immunological and expression enhancing fusion partners. Other fusion partners may be selected so as to increase the solubility of the protein or to enable the protein to be targeted to desired intracellular compartments. Still further fusion partners include affinity tags, which facilitate purification of the protein.

Fusion proteins may generally be prepared using standard techniques, including chemical conjugation. Preferably, a fusion protein is expressed as a recombinant protein, allowing the production of increased levels, relative to a non-fused protein, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and second polypeptide components by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad. Sci. USA* 83:8258–8262, 1986; U.S. Pat. Nos. 4,935,233 and 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

Within preferred embodiments, an immunological fusion partner is derived from protein D, a surface protein of the gram-negative bacterium Haemophilus influenza B (See, e.g., WO 91/18926, U.S. Pat. Nos. 6,139,846, 6,025,484, 5,989,828, 5,888,517, and 5,858,677). Preferably, a protein D derivative comprises approximately the first third of the protein (e.g. the first N-terminal 100–110 amino acids), and a protein D derivative may be lipidated. Within certain preferred embodiments, the first 109 residues of a Lipoprotein D fusion partner is included on the N-terminus to provide the polypeptide with additional exogenous T-cell epitopes and to increase the expression level in *E. coli* (thus functioning as an expression enhancer). The lipid tail ensures optimal presentation of the antigen to antigen presenting cells. Other fusion partners include the non-structural protein from influenzae virus, NS1 (hemagglutinin). Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; *Gene* 43:265–292, 1986). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see, *Biotechnology* 10:795–798, 1992). Within a preferred embodiment, a repeat portion of LYTA may be incorporated into a fusion protein. A repeat portion is found in the C-terminal region starting at residue 178. A particularly preferred repeat portion incorporates residues 188–305.

In another embodiment of the invention, the adjuvant system described herein is used in the preparation of DNA-based vaccine compositions. Illustrative vaccines of this type contain DNA encoding one or more polypeptide antigens, such that the antigen is generated in situ. The DNA may be present within any of a variety of delivery systems known to those of ordinary skill in the art, including nucleic acid expression systems, bacteria and viral expression systems. Numerous gene delivery techniques are well known in the art, such as those described by Rolland, *Crit. Rev. Therap. Drug Carrier Systems* 15:143–198, 1998, and references cited therein. Appropriate nucleic acid expression systems contain the necessary DNA sequences for expression in the patient (such as a suitable promoter and terminating signal). Bacterial delivery systems involve the administration of a bacterium (such as Bacillus-Calmette-Guerrin) that expresses an immunogenic portion of the polypeptide on its cell surface or secretes such an epitope. In one preferred embodiment, the DNA is introduced using a viral expression system (e.g., vaccinia or other pox virus, retrovirus, or adenovirus), which typically involves the use of a non-pathogenic (defective), replication competent virus. Illustrative systems are disclosed, for example, in Fisher-Hoch et al., *Proc. Natl. Acad. Sci. USA* 86:317–321, 1989; Flexner et al., *Ann. N.Y. Acad. Sci.* 569:86–103, 1989; Flexner et al., *Vaccine* 8:17–21, 1990; U.S. Pat. Nos. 4,603, 112, 4,769,330, and 5,017,487; WO 89/01973; U.S. Pat. No. 4,777,127; GB 2,200,651; EP 0,345,242; WO 91/02805; Berkner, *Biotechniques* 6:616–627, 1988; Rosenfeld et al., *Science* 252:431–434, 1991; Kolls et al., *Proc. Natl. Acad. Sci. USA* 91:215–219, 1994; Kass-Eisler et al., *Proc. Natl. Acad. Sci. USA* 90:11498–11502, 1993; Guzman et al., *Circulation* 88:2838–2848, 1993; and Guzman et al., *Cir. Res.* 73:1202–1207, 1993. Techniques for incorporating DNA into such expression systems are well known to those of ordinary skill in the art.

Alternatively, the DNA may be "naked," as described, for example, in Ulmer et al., *Science* 259:1745–1749, 1993 and reviewed by Cohen, *Science* 259:1691–1692, 1993. The uptake of naked DNA may be increased by coating the DNA onto biodegradable beads that are efficiently transported into the cells. It will be apparent that a vaccine may comprise both a polynucleotide and a polypeptide component if desired.

Moreover, it will be apparent that a vaccine may contain pharmaceutically acceptable salts of the desired polynucleotide, polypeptide and/or carbohydrate antigens. For example, such salts may be prepared from pharmaceutically acceptable non-toxic bases, including organic bases (e.g., salts of primary, secondary and tertiary amines and basic amino acids) and inorganic bases (e.g., sodium, potassium, lithium, ammonium, calcium and magnesium salts).

The adjuvant system of the present invention exhibits strong adjuvant effects when administered over a wide range of dosages and a wide range of ratios.

The amount of antigen in each vaccine dose is generally selected as an amount which induces an immunoprotective response without significant adverse side effects in typical vaccines. Such amount will vary depending upon which specific immunogen is employed and how it is presented. Generally, it is expected that each dose will comprise about 1–1000 $\mu$g of protein, most typically about 2–100 $\mu$g, preferably about 5–50 $\mu$g. Of course, the dosage administered may be dependent upon the age, weight, kind of concurrent treatment, if any, and nature of the antigen administered.

The immunogenic activity of a given amount of a vaccine composition of the present invention can be readily determined, for example by monitoring the increase in titer of antibody against the antigen used in the vaccine composition (Dalsgaard, K. Acta Veterinia Scandinavica 69:1–40 (1978)). Another common method involves injecting CD-1 mice intradermally with various amounts of a vaccine composition, later harvesting sera from the mice and testing for anti-immunogen antibody, e.g., by ELISA. These and other similar approaches will be apparent to the skilled artisan.

The antigen can be derived and/or isolated from essentially any desired source depending on the infectious disease, autoimmune disease, condition, cancer, pathogen, or a disease that is to be treated with a given vaccine composition. By way of illustration, the antigens can be derived from viral sources, such as influenza virus, feline leukemia virus, feline immunodeficiency virus, Human HIV-1, HIV-2, Herpes Simplex virus type 2, Human cytomegalovirus, Hepatitis A, B, C or E, Respiratory Syncytial virus, human papilloma virus rabies, measles, or hoof and mouth disease viruses. Illustrative antigens can also be derived from bacterial sources, such as anthrax, diphtheria, Lyme disease, malaria, tuberculosis, Leishmaniasis, T. cruzi, Ehrlichia, Candida etc., or from protozoans such as Babeosis bovis or Plasmodium. The antigen(s) will typically be comprised of natural or synthetic amino acids, e.g., in the form of peptides, polypeptides, or proteins, can be comprised of polysaccharides, or can be mixtures thereof. Illustrative antigens can be isolated from natural sources, synthesized by means of solid phase synthesis, or can be obtained by way of recombinant DNA techniques.

In another embodiment, tumor antigens are used in the vaccine compositions of the present invention for the prophylaxis and/or therapy of cancer. Tumor antigens are surface molecules that are differentially expressed in tumor cells relative to non-tumor tissues. Tumor antigens make tumor cells immunologically distinct from normal cells and provide diagnostic and therapeutic targets for human cancers. Tumor antigens have been characterized either as membrane proteins or as altered carbohydrate molecules of glycoproteins or glycolipids on the cell surface. Cancer cells often have distinctive tumor antigens on their surfaces, such as truncated epidermal growth factor, folate binding protein, epithelial mucins, melanoferrin, carcinoembryonic antigen, prostate-specific membrane antigen, HER2-neu, which are candidates for use in therapeutic cancer vaccines. Because tumor antigens are normal or related to normal components of the body, the immune system often fails to mount an effective immune response against those antigens to destroy the tumor cells. To achieve such a response, the adjuvant systems described herein can be utilized. As a result, exogenous proteins can enter the pathway for processing endogenous antigens, leading to the production of cytolytic or cytotoxic T cells (CTL). This adjuvant effect facilitates the production of antigen specific CTLs which seek and destroy those tumor cells carrying on their surface the tumor antigen (s) used for immunization. Illustrative cancer types for which this approach can be used include prostate, colon, breast, ovarian, pancreatic, brain, head and neck, melanoma, leukemia, lymphoma, etc.

In one embodiment, the antigen present in the vaccine composition is not a foreign antigen, but a self antigen, i.e., the vaccine composition is directed toward an autoimmune disease. Examples of autoimmune diseases include type 1 diabetes, conventional organ specific autoimmunity, neurological disease, rheumatic diseases/connective tissue disease, autoimmune cytopenias, and related autoimmune diseases. Such conventional organ specific autoimmunity may include thyroiditis (Graves+Hashimoto's), gastritis, adrenalitis (Addison's), ovaritis, primary biliary cirrhosis, myasthenia gravis, gonadal failure, hypoparathyroidism, alopecia, malabsorption syndrome, pernicious anemia, hepatitis, anti-receptor antibody diseases and vitiligo. Such neurological diseases may include schizophrenia, Alzheimer's disease, depression, hypopituitarism, diabetes insipidus, sicca syndrome and multiple sclerosis. Such rheumatic diseases/connective tissue diseases may include rheumatoid arthritis, systemic lupus erythematous (SLE) or Lupus, scleroderma, polymyositis, inflammatory bowel disease, dermatomyositis, ulcerative colitis, Crohn's disease, vasculitis, psoriatic arthritis, exfoliative psoriatic dermatitis, pemphigus vulgaris, Sjögren's syndrome. Other autoimmune related diseases may include autoimmune uvoretinitis, glomerulonephritis, post myocardial infarction cardiotomy syndrome, pulmonary hemosiderosis, amyloidosis, sarcoidosis, aphthous stomatitis, and other immune related diseases, as presented herein and known in the related arts.

In one embodiment, the antigen is covalently bonded to an adjuvant such as the compound of Formula I to produce a discrete molecule which exhibits a surprisingly unexpected enhanced adjuvanting effect on the antigen which is greater than the adjuvanting effect attainable in the absence of such covalent bonding, as in a mixture of the two components (i.e., the antigen and the compound of Formula I). The covalent bonding can be achieved by reaction through functional groups; for example in the case of the compound of Formula I through the carboxylic acid group, the hydroxyl group or the aldehyde functionality. A further enhanced adjuvanting effect may be attained for such covalently-bonded antigen by incorporating a mineral salt adjuvant with such compounds. The mineral salt adjuvant preferably comprises aluminum hydroxide or aluminum phosphate, although other known mineral salt adjuvants, such as calcium phosphate, zinc hydroxide or calcium hydroxide, may be used.

In one embodiment, the adjuvant of the present vaccine composition comprises a suspension of water or an aqueous solution, wherein the suspension or solution comprises the compound of Formula I.

In one embodiment, the suspension comprising the compound of Formula I is in the form of an emulsion, such as a water-in-oil emulsion or an oil-in-water emulsion. Suitable surfactants well known to those skilled in the art may be used in such emulsions. In one embodiment, the suspension comprising the compound of Formula I is in the form of a micellar dispersion comprising at least one suitable surfactant. The surfactants useful in such micellar dispersions include phospholipids. Examples of phospholipids include: diacyl phosphatidyl glycerols, such as: dimyristoyl phosphatidyl glycerol (DPMG), dipalnitoyl phosphatidyl glycerol (DPPG), and distearoyl phosphatidyl glycerol (DSPG); diacyl phosphatidyl cholines, such as: dimyristoyl phosphatidylcholine (DPMC), dipalmitoyl phosphatidylcholine (DPPC), and distearoyl phosphatidylcholine (DSPC); diacyl phosphatidic acids, such as: dimyristoyl phosphatidic acid (DPMA), dipalmitoyl phosphatidic acid (DPPA), and distearoyl phosphatidic acid (DSPA); and diacyl phosphatidyl ethanolamines such as: dimyristoyl phosphatidyl ethanolamine (DPME), dipalmitoyl phosphatidyl ethanolamine (DPPE), and distearoyl phosphatidyl ethanolamine (DSPE). Other examples include, but are not limited to, derivatives of ethanolamine (such as phosphatidyl ethanolamine, as mentioned above, or cephalin), serine (such as phosphatidyl serine) and 3'-O-lysyl glycerol (such as 3'-O-lysyl-phosphatidylglycerol).

Typically, a surfactant:adjuvant molar ratio in an aqueous formulation will be from about 10:1 to about 1:10, more typically from about 5:1 to about 1:5, however any effective amount of surfactant may be used in an aqueous formulation to best suit the specific objectives of interest.

The adjuvant may include other polynucleotides and/or polypeptides. It will be apparent that a vaccine may contain pharmaceutically acceptable salts of the polynucleotides and polypeptides provided herein. Such salts may be prepared from pharmaceutically acceptable non-toxic bases, including organic bases (e.g., salts of primary, secondary and tertiary amines and basic amino acids) and inorganic bases (e.g., sodium, potassium, lithium, ammonium, calcium and magnesium salts).

While any suitable carrier known to those of ordinary skill in the art may be employed in the pharmaceutical compositions of this invention, the type of carrier will vary depending on the mode of administration. The vaccine compositions of the present invention may be formulated for any appropriate manner of administration, including for example, topical, oral, nasal, intravenous, intravaginal, epicutaneous, sublingual, intracranial, intradermal, intraperitoneal, subcutaneous, intramuscular administration, or via inhalation. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268; 5,075,109; 5,928,647; 5,811,128; 5,820,883; 5,853,763; 5,814,344 and 5,942,252, the disclosures of which are incorporated herein by reference in their entireties. Modified hepatitis B core protein carrier systems are also suitable, such as those described in WO 99/40934, and references cited therein, all incorporated herein by reference. One can also employ a carrier comprising particulate-protein complexes, such as those described in U.S. Pat. No. 5,928,647, the disclosure of which is incorporated herein by reference in its entirety, which are capable of inducing a class I-restricted cytotoxic T lymphocyte responses in a host.

In one illustrative embodiment, the vaccine formulations are administered to the mucosae, in particular to the oral cavity, and preferably to a sublingual site, for eliciting an immune response. Oral cavity administration may be preferred in many instances over traditional parenteral delivery due to the ease and convenience offered by noninvasive administration techniques. Moreover, this approach further provides a means for eliciting mucosal immunity, which can often be difficult to achieve with traditional parenteral delivery, and which can provide protection from airborne pathogens and/or allergens. An additional advantage of oral cavity administration is that patient compliance may be improved with sublingual vaccine delivery, especially for pediatric applications, or for applications traditionally requiring numerous injections over a prolonged period of time, such as with allergy desensitization therapies.

The vaccine compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, vaccine compositions of the present invention may be formulated as a lyophilisate. Compounds may also be encapsulated within liposomes using well known technology.

The vaccine compositions of the present invention may also comprise other adjuvants or immunoeffectors. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham); mineral salts (for example, aluminum, silica, kaolin, and carbon); aluminum salts such as aluminum hydroxide gel (alum), $AlK(SO_4)_2$, $AlNa(SO_4)_2$, $AlNH_4(SO_4)$, and $Al(OH)_3$; salts of calcium (e.g, $Ca_3(PO_4)_2$), iron or zinc; an insoluble suspension of acylated tyrosine; acylated sugars; cationically or anionically derivatized polysaccharides; polynucleotides (for example, poly IC and poly AU acids); polyphosphazenes; cyanoacrylates; polymerase-(DL-lactide-co-glycoside); biodegradable microspheres; liposomes ; lipid A and its derivatives; monophosphoryl lipid A; wax D from Mycobacterium tuberculosis, as well as substances found in Corynebacterium parvum, Bordetella pertussis, and members of the genus Brucella); bovine serum albumin; diphtheria toxoid; tetanus toxoid; edestin; keyhole-limpet hemocyanin; Pseudomonal Toxin A; choleragenoid; cholera toxin; pertussis toxin; viral proteins; and quil A. Aminoalkyl glucosamine phosphate compounds can also be used (see, e.g., WO 98/50399, U.S. Pat. No. 6,113,918 (which issued from U.S. Ser. No. 08/853,826), and U.S. Ser. No. 09/074,720). In addition, adjuvants such as cytokines (e.g., GM-CSF or interleukin-2, -7, or -12), interferons, or tumor necrosis factor, may also be used as adjuvants. Protein and polypeptide adjuvants may be obtained from natural or recombinant sources according to methods well known to those skilled in the art. When obtained from recombinant sources, the adjuvant may comprise a protein fragment comprising at least the immunostimulatory portion of the molecule. Other known immunostimulatory macromolecules which can be used in the practice of the invention include, but are not limited to, polysaccharides, tRNA, non-metabolizable synthetic polymers such as polyvinylamine, polymethacrylic acid, polyvinylpyrrolidone, mixed polycondensates (with relatively high molecular weight) of 4',4-diaminodiphenylmethane-3,3'-dicarboxylic acid and 4-nitro-2-aminobenzoic acid (See, Sela, M., Science 166: 1365–1374 (1969)) or glycolipids, lipids or carbohydrates.

Within the vaccine compositions provided herein, the adjuvant composition is preferably designed to induce an immune response predominantly of the Th1 type. High levels of Th1-type cytokines (e.g., IFN-γ, TNF-α, IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see, Mosmann and Coffinan, *Ann. Rev. Immunol.* 1989, 7: 145–173.

Preferred adjuvants for use in eliciting a predominantly Th1-type response include, for example, a combination of monophosphoryl lipid A, preferably 3-de-O-acylated monophosphoryl lipid A (3D-MPL), together with an aluminum salt. MPL adjuvants are available from Corixa Corporation (Hamilton, Mont.; see, U.S. Pat. Nos. 4,436,727; 4,877,611; 4,866,034 and 4,912,094). CpG-containing oligonucleotides (in which the CpG dinucleotide is umnethylated) also induce a predominantly Th1 response. Such oligonucleotides are well known and are described, for example, in WO 96/02555, WO 99/33488, U.S. Pat. Nos. 6,008,200 and 5,856,462. Immunostimulatory DNA sequences are also described, for example, by Sato et al., Science 1996 273: 352–354. Another preferred adjuvant is a saponin, preferably QS21 (Aquila, United States), which may be used alone or in combination with other adjuvants. For example, an enhanced system involves the combination of a monophosphoryl lipid A and saponin derivative, such as the combination of QS21 and 3D-MPL as described in WO 94/00153, or a less reactogenic composition where the QS21 is quenched with cholesterol, as described in WO 96/33739. Other preferred formulations comprise an oil-in-water emulsion and tocopherol. A particularly potent adjuvant formulation involving QS21, 3D-MPL and tocopherol in an oil-in-water emulsion is described in WO 95/17210.

Other preferred adjuvants include Montanide ISA 720 (Seppic, France), SAF (Chiron, Calif., United States), ISCOMS (CSL), MF-59 (Chiron), the SBAS series of adjuvants (e.g., SBAS-2 or SBAS-4, available from SmithKline Beecham, Rixensart, Belgium), Detox™ (Corixa Corporation, Hamilton, Mont.), 2-[(R)-3-tetradecanoyloxytetradecanoylamino]ethyl 2-Deoxy-4-O-phosphono-3-O-[(R)-3-tetradecanoyloxytetradecanoyl]-2-[(R)-3-tetradecanoyloxytetradecanoylamino]-β-D-glucopyranoside triethylammonium salt (compound 99) and other aminoalkyl glucosaminide 4-phosphates (AGPs). The synthesis of compound 99 and other AGP's has been described previously (see e.g., Johnson et al. (1999) Bioorg. Med. Chem. Lett. 9: 2273–2278; PCT/WO98/50399; and U.S. Pat. No. 6,113,918). AGPs typically consist of an acylated glucose moiety linked to an acylated aminoalkyl group (see e.g., Johnson et al. (1999) Bioorg. Med. Chem. Lett. 9: 2273–2278; PCT/WO98/50399; and U.S. Pat. No. 6,113,918).

The compositions described herein may be administered as part of a sustained release formulation (i.e., a formulation such as a capsule, sponge or gel (composed of polysaccharides, for example) that effects a slow release of compound following administration). Such formulations may generally be prepared using well known technology (see, e.g., Coombes et al., Vaccine 14:1429–1438, 1996) and administered by, for example, oral, rectal or subcutaneous implantation, or by implantation at the desired target site. Sustained-release formulations may contain a polypeptide, polynucleotide or antibody dispersed in a carrier matrix and/or contained within a reservoir surrounded by a rate controlling membrane. Carriers for use within such formulations are biocompatible, and may also be biodegradable; preferably the formulation provides a relatively constant level of active component release. Such carriers include microparticles of poly(lactide-co-glycolide), polyacrylate, latex, starch, cellulose, dextran and the like. Other delayed-release carriers include supramolecular biovectors, which comprise a non-liquid hydrophilic core (e.g., a cross-linked polysaccharide or oligosaccharide) and, optionally, an external layer comprising an amphiphilic compound, such as a phospholipid (see, e.g., U.S. Pat. No. 5,151,254 and PCT applications WO 94/20078, WO/94/23701 and WO 96/06638). The amount of active compound contained within a sustained release formulation will vary depending upon the site of implantation, the rate and expected duration of release and the nature of the condition to be treated or prevented.

Any of a variety of known delivery vehicles may be employed within pharmaceutical compositions and vaccines to facilitate production of an antigen-specific immune response that targets cells. Delivery vehicles include antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have anti-target effects per se and/or to be immunologically compatible with the receiver (i.e., matched HLA haplotype). APCs may generally be isolated from any of a variety of biological fluids and organs, including tumor and peritumoral tissues, and may be autologous, allogeneic, syngeneic or xenogeneic cells.

Certain preferred embodiments of the present invention use dendritic cells or progenitors thereof as antigen-presenting cells. Dendritic cells are highly potent APCs (Banchereau and Steinman, Nature 392:245–251, 1998) and have been shown to be effective as a physiological adjuvant for eliciting prophylactic or therapeutic antitumor immunity (see, Timmerman and Levy, Ann. Rev. Med. 50:507–529, 1999). In general, dendritic cells may be identified based on their typical shape (stellate in situ, with marked cytoplasmic processes (dendrites) visible in vitro), their ability to take up, process and present antigens with high efficiency and their ability to activate naïve T cell responses. Dendritic cells may, of course, be engineered to express specific cell-surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within a vaccine (see, Zitvogel et al., Nature Med. 4:594–600, 1998).

Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce differentiation, maturation and proliferation of dendritic cells.

Dendritic cells are conveniently categorized as "immature" and "mature" cells, which allows a simple way to discriminate between two well characterized phenotypes. However, this nomenclature should not be construed to exclude all possible intermediate stages of differentiation. Immature dendritic cells are characterized as APC with a high capacity for antigen uptake and processing, which correlates with the high expression of Fcγ receptor and mannose receptor. The mature phenotype is typically characterized by a lower expression of these markers, but a high expression of cell surface molecules responsible for T cell activation such as class I and class II MHC, adhesion molecules (e.g., CD54 and CD11) and costimulatory molecules (e.g., CD40, CD80, CD86 and 4-1BB).

APCs may generally be transfected with a polynucleotide encoding an antigen polypeptide (or portion or other variant thereof) such that the antigen polypeptide, or an immunogenic portion thereof, is expressed on the cell surface. Such transfection may take place ex vivo, and a composition or vaccine comprising such transfected cells, and the adjuvants described herein, may then be used for therapeutic purposes. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al., *Immunology and cell Biology* 75: 456–460, 1997. Antigen loading of dendritic cells may be achieved by incubating dendritic cells or progenitor cells with the antigen polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide.

In one embodiment, the vaccine composition comprises a liposome vesicle comprising the compound of Formula I. Liposomes are generally produced from phospholipids or other lipid substances. Procedures for the preparation of liposomes are well known to those of skill in the art. Any lipid capable of forming vesicles that comprises the compound of Formula I can be employed. For clinical application, it is desirable that the lipid be non-toxic, physiologically acceptable, and metabolizable. Common bilayer forming lipids having clinical potential are phospholipids, fatty acids, sphingolipids, glycosphingolipids, and steroids. Glycerol containing phospholipids are the most commonly used component of liposome formulations having clinical utility. One commonly used example is phosphatidylcholine or lecithin. The steroid cholesterol and its derivatives are often included as components of liposomal membranes. The tendency of liposomes to aggregate and fuse can be controlled by the inclusion of small amounts of acidic or basic lipids in the formulation. The properties of liposomes containing phospholipids are determined by the chemistry of the phospholipid. Important considerations are the hydrocarbon chain length, degree of unsaturation of the hydrocarbon chain, degree of branching of the hydrocarbon chain, and temperature of the system.

Multilamellar liposomes can be created by depositing a mixture of lipids as a thin film by evaporation under reduced pressure followed by dispersion with an excess volume of aqueous buffer containing the antigen with or without organic solvents. Another method is to mix the aqueous phase containing the antigen with small unilamellar liposomes followed by lyophilization. The multilamellar liposomes are formed when the lyophilized product is rehydrated, usually with a small amount of distilled water. The small unilamellar liposomes to be used in this process are produced by dispersing the lipids in an aqueous medium followed by a mechanical means of dispersion such as sonication, use of a high pressure device, or a solvent injection method. Large and intermediate sized unilamellar liposomes can also be produced by conventional techniques including detergent dialysis, extrusion through small pore size membranes under high pressure, freeze thawing followed by slow swelling, dehydration followed by rehydration and dilution, or dialysis of lipids in the presence of chaotropic ions. The size of the liposomes can be made more uniform by fractionation procedures such as centrifugation or size exclusion chromatography, homogenization, or capillary pore membrane extrusion.

Methods for Inducing or Enhancing Immunogenicity and for Treating or Preventing Disease In one aspect, the present invention provides a method for inducing or enhancing immunogenicity of an antigen in a mammal comprising administering to the mammal a vaccine composition comprising the antigen and an effective amount of a vaccine adjuvant composition comprising the compound of Formula I. As used in this context, the "vaccine adjuvant composition" includes any composition comprising the compound of Formula I that enhances an immune response to an exogenous antigen. Such "vaccine adjuvant composition" includes biodegradable microspheres (e.g., polylactic galactide) and liposomes. See, e.g., Fullerton, U.S. Pat. No. 4,235,877. Vaccine preparation is generally described in, for example, M. F. Powell and M. J. Newman, eds., "Vaccine Design (the subunit and adjuvant approach)," Plenum Press (NY, 1995). Vaccines may be designed to generate antibody immunity and/or cellular immunity.

The vaccine compositions of the present invention may be administered in any appropriate manner of administration, including for example, topical, oral, nasal, intravenous, intravaginal, epicutaneous, sublingual, intracranial, intraperitoneal, subcutaneous, intramuscular administration, or via inhalation, as disclosed supra.

In one aspect, the present invention provides a method of treating or preventing a disease in a mammal comprising administering to said mammal a vaccine composition comprising an antigen and an effective immunopotentiatory amount of the compound of Formula I. The diseases include cancer, autoimmune disease, allergy and infectious disease (such as bacterial and viral infection). In one embodiment, the effective amount of the compound of Formula I ranges from 0.0001 to about 1.0 mg/kg of body weight of the subject mammal, more preferably from 0.001 to 0.1 to about 0.1 mg/kg of body weight of the mammal. In one embodiment, the compound of Formula I is administered once weekly to once monthly for a period of up to 6 months, more preferably once monthly for a period of about 2–3 months.

EXAMPLES

The following examples are offered to illustrate, but not to limit the claimed invention.

Example 1

Preparation of Methyl 4-(3-Formyl-4-hydroxyphenoxymethyl)benzoate (Isotucaresol Methyl Ester, compound 40)

The following example illustrates the ortho-debenzylation of 2,5-di-(4-methoxycarbonylphenylmethoxy)benzaldehyde to form methyl 4-(3-formyl-4-hydroxyphenoxymethyl) benzoate (Isotucaresol Methyl Ester; 40).

A solution of 2,5-di-(4-methoxycarbonylphenylmethoxy) benzaldehyde (39) (34.4 g, 0.0792 mol) in anhydrous $CH_2Cl_2$ (1.5 L) at 5° C. under argon was treated dropwise with $BCl_3 \cdot S(CH_3)_2$ (2.0 M in $CH_2Cl_2$; 43.5 ml, 0.087 mole) over 25 min. The resulting reddish-orange solution was stirred at 5° C. for 1.5 h and then allowed to stir and warm to room temperature over 2 h. The mixture was recooled to 5° C., treated dropwise with additional $BCl_3 \cdot S(CH_3)_2$ (16 ml, 0.032 mol) over 10 min, and then allowed to stir and warm to ambient temperature overnight (17 h). The dark reddish-orange reaction mixture was quenched with ice-cold 1 N aq HCl (750 ml), stirred vigorously for 5 min, and the layers were separated. The aqueous phase was extracted with $CH_2Cl_2$ (100 ml) and the combined organic layers were washed with saturated aq $NaHCO_3$ (750 ml). The resulting light-orange solution was dried ($Na_2SO_4$), decolorized with Norit B, and filtered through a short pad of Celite and silica gel. The pad was rinsed with 25% EtOAc-hexanes (500 ml) and the combined filtrate and rinsings were concentrated to give 21.9 (97%) of a light yellow solid. The partially purified product was recrystallized from EtOAc/cyclohexane to give 19.5 g (86%) of methyl 4-(3-formyl-4-hydroxyphenoxymethyl)benzoate (isotucaresol methyl ester) (40) as fluffy light-yellow needles: mp 132–134° C.; $R_f$ 0.45 (30% EtOAc-hexanes); $^1$H NMR (300 MHz, $CDCl_3$) δ10.66 (s, 1H, CHO), 9.82 (s, 1H, OH), 8.06 (d, 2H, J=8.2 Hz, H-2,6), 7.49 (d, 2H, J=8.2 Hz, H-3,5), 7.21 (dd, 1H, J=3.0, 8.9 Hz, H-6'), 7.05 (d, 1H, J=3.0 Hz, H-2'), 6.94 (d, 1H, J=8.9 Hz), 5.11 (s, 2H, $CH_2$), 3.92 (s, 3H, $CH_3$); $^{13}$C NMR (75 MHz, $CDCl_3$) δ195.8, 166.6, 156.3, 151.4, 141.6, 129.9, 126.9, 125.9, 120.0, 118.8, 116.8, 70.3, 52.2; HRMS calcd. for $M+NH_4^+$ 304.1185, found 304.1193; Anal. calcd. for $C_{16}H_{14}O_5$: C, 67.13; H, 4.93. Found: C, 67.00; H, 5.03.

Example 2

Preparation of 4-[(4-carboxymethoxy-3-formyl-phenoxy)methyl]benzoic acid

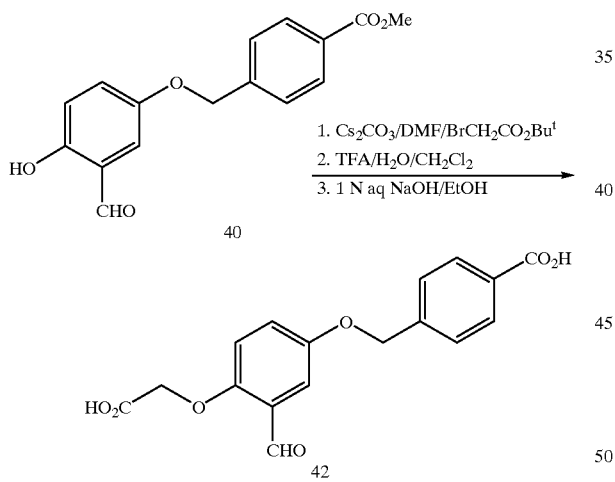

(1) A solution of methyl 4-[(3-formyl-4-hydroxyphenoxy)methyl]benzoate (40; 1.00 g, 3.49 mmol) and t-butyl bromoacetate (0.62 mL. 4.19 mmol) in anhydrous dimethylformamide (DMF; 10 mL) at 25° C. under argon was treated with cesium carbonate (1.71 g, 5.24 mmol). The resulting light-yellow suspension was stirred overnight at 25° C. and poured into $H_2O$ (100 mL). The white precipitate which formed was collected, washed with $H_2O$ (2×10 mL), and dried under high vacuum to give 1.29 g (92%) of methyl 4-[(4-t-butyloxycarbonyhnethoxy-3-formyl)methyl]benzoate as a colorless powder: mp 106–107.5° C.; $R_f$ 0.41 (30% EtOAc-hexanes); $^1$H NMR (300 MHz, $CDCl_3$) δ10.52 (s, 1H, CHO), 8.05 (d, 2H, J=8.2 Hz, H-2,6), 7.48 (d, 2H, J=8.2 Hz, H-3,5), 7.42 (d, 1H, J=3.0 Hz, H-2'), 7.18 (dd, J=3.0, 8.2 Hz, H-6'), 6.83 (d, 1H, J=8.2 Hz, H-5'), 5.11 (s, 2H, —$OCH_2Ar$), 4.60 (s, 2H, —$OCH_2CO_2$—), 3.92 (s, $CH_3$), 1.47 (s, 9H, t-Bu); $^{13}$C NMR (75 MHz, $CDCl_3$) δ189.2, 167.3, 166.7, 155.2, 153.0, 141.6, 129.8, 127.0, 125.7, 123.8, 114.6, 111.8, 82.8, 69.9, 66.7, 52.1, 28.1; HRMS calcd for $[M+NH_4]^+$ 418.1866, found 418.1880.

(2) A solution of the compound prepared in (1) above (1.20 g, 3.00 mmol) in $CH_2Cl_2$—$CF_3CO_2H$—$H_2O$ (7:7:0.5; 15 mL) was stirred at 25° C. for 3.5 h. The resulting solution was concentrated and the residual $CF_3CO_2H$ azeotroped with benzene. The off-white solid obtained was dissolved in 1:1 1N aq NaOH-EtOH (23 mL) and stirred at 25° C. overnight. Additional 1N aq NaOH (5 mL) was added and the solution was stirred for 3 h at 25° C. and then acidified with conc HCl (~1 mL). The light-yellow precipitate which formed was collected, washed with $H_2O$ (3×15 mL), and dried under high vacuum to give 0.85 g (86%) of partially purified product. A portion of this material (0.61 g) was crystallized from MeCN-EtOAc to give 0.395 g (66%) of 4-[(4-carboxymethoxy-3-formyl-phenoxy)methyl]benzoic acid (42) as an off-white solid: Mp 239–242° C. (dec); $R_f$ 0.2 ($CHCl_3$—MeOH—AcOH, 80:20:0.5); $^1$H NMR (300 MHz, DMSO-$d_6$) δ13.05 (br s, 2H, 2 $CO_2H$), 10.39 (s, 1H, CHO), 7.95 (d, 2H, J=8.1 Hz, H-2,6), 7.55 (d, 2H, J=8.1 Hz, H-3,5), 7.33 (dd, 1H, J=3.1, 9.1 Hz, H-6'), 7.26 (d, 1H, J=3.1 Hz, H-2'), 7.15, (d, 1H, J=9.1 Hz, H-5'), 5.21 (s, 2H, —$OCH_2Ar$), 4.84 (s, 2H, —$OCH_2CO_2H$; $^{13}$C NMR (75 MHz, DMSO-$d_6$) δ188.8, 169.9, 166.9, 155.0, 152.4, 141.9, 130.0, 129.4, 127.2, 124.9, 123.7, 115.9, 111.2, 69.1, 65.8; HRMS calcd for $[M+NH_4]^+$ 348.1083, found 348.1093; Anal. Calcd for $C_{17}H_{14}O_7$: C, 61.82; H, 4.27. Found: C, 61.84; H, 4.42.

Example 3

Preparation of 4-[4-(3-carboxypropoxy)-3-formyl-phenoxy)methyl]benzoic acid)

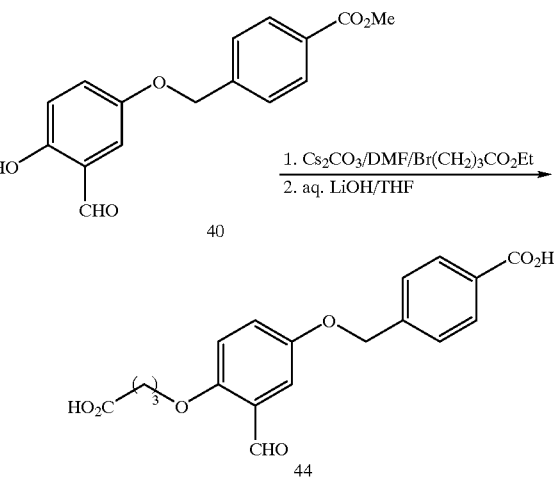

(1) In the same manner as described in Example 2, methyl 4-[(3-formyl-4-hydroxyphenoxy)methyl]benzoate (40; 0.62 g, 2.16 mmol) was alkylated with ethyl 4-bromobutyrate (0.39 mL, 2.7 mmol) to give 0.725 g (84%) of 4-([4-(3-ethoxycarbonylpropoxy)-3-formyl-phenoxy]methyl)benzoate as a colorless powder: mp 106–107.5° C.; $R_f$ 0.41 (30% EtOAc-hexanes); $^1$H NMR (300 MHz, $CDCl_3$) δ10.44 (s, 1H, CHO), 8.05 (d, 2H, J=8.0 Hz, H-2,6), 7.49 (d, 2H, J=8.0 Hz, H-3,5), 7.39 (d, 1H, J=3.0 Hz, H-2'), 7.18 (dd, J=3.0, 9.1 Hz, H-6'), 6.94

(d, 1H, J=9.1 Hz, H-5'), 5.11 (s, 2H, —OCH$_2$Ar), 4.14 (q, 2H, J=7.1 Hz, CH$_3$CH$_2$O—), 4.10 (t, 2H, J=6 Hz, OCH$_2$CH$_2$—), 3.92 (s, 3H, CH$_3$O—), 2.53 (t, 2H, J=7.1 Hz, —CH$_2$CO$_2$—), 2.16 (m, 2H.—CH$_2$CH$_2$CH$_2$—), 1.26 (s, 3H, CH$_3$CH$_2$—); $^{13}$C NMR (75 MHz, CDCl$_3$) δ189.1, 172.8, 166.7, 156.2, 152.4, 141.8, 129.8, 127.0, 125.1, 124.1, 114.3, 111.7, 69.9, 68.0, 60.6, 52.1, 30.7, 24.6, 14.2; HRMS calcd for [M+NH$_4$]$^+$ 418.1866, found 418.1853.

(2) A solution of the compound prepared in (1) above (0.600 g, 1.50 mmol) in tetrahydrofuran (6 mL) was treated with aq LiOH (2.5 N; 2.0 mL, 5.0 mmol) and stirred at 25° C. overnight. The resulting biphasic reaction mixture was diluted with H$_2$O (75 mL), washed with Et$_2$O (25 mL), and acidified with conc HCl (~0.75 mL). The fine suspension which formed was extracted with EtOAc (3×300 mL) and the combined EtOAc layers were dried (Na$_2$SO$_4$) and concentrated to give 0.54 g (100%) of pure product as an off-white powder (mp 234–236° C. (dec); Anal. Calcd for C$_{19}$H$_{18}$O$_7$: C, 63.68; H, 5.06. Found: C, 63.52; H, 5.16). A portion of this material (0.3 g) was crystallized from MeCN-EtOAc to give 0.23 g (77%) of 4-[4-(3-carboxypropoxy)-3-formyl-phenoxy)methyl]benzoic acid (44) as a cream-colored solid: mp 234.5–237° C. (dec); R$_f$ 0.54 (CHCl$_3$—MeOH—AcOH, 90:10:0.5); $^1$H NMR (300 MHz, DMSO-d$_6$) δ12.53 (br s, 2H, 2 CO$_2$H), 10.33 (s, 1H, CHO), 7.95 (d, 2H, J=8.0 Hz, H-2,6), 7.55 (d, 2H, J=8.0 Hz, H-3,5), 7.33 (dd, 1H, J=3.0, 9.1 Hz, H-6'), 7.25 (d, 1H, J=3.0 Hz, H-2'), 7.18, (d, 1H, J=9.1 Hz, H-5'), 5.20 (s, 2H, —OCH$_2$Ar), 4.10 (t, 2H, J=6.0 Hz, —OCH$_2$CH$_2$—), 2.53 (t, 2H, J=7.0 Hz, —CH$_2$CO$_2$—), 1.99 (m, 2H. —CH$_2$CH$_2$CH$_2$—); $^{13}$C NMR (75 MHz, DMSO-d$_6$) δ188.8, 174.0, 166.9, 155.6, 151.8, 141.9, 130.0, 129.4, 127.2, 124.5, 123.9, 115.2, 111.4, 69.1, 68.1, 30.3, 24.2; HRMS calcd for [M+NH$_4$]$^+$ 376.1396, found 376.1389; Anal. Calcd for C$_{19}$H$_{18}$O$_7$: C, 63.68; H, 5.06. Found: C, 63.45; H, 5.06.

Example 4

Preparation of 1-O-[4-(4-carboxyphenylmethoxy)-2-formylphenyl]-β-D-glucupyranosiduronic acid (isotucaresol D-glucuronide 4-([3-formyl-4-(β-D-glucopyranosyloxyuronic acid)phenoxy]methyl)benzoic acid, compound 4)

(1) A solution of acetobromo-α-D-glucuronic acid methyl ester (0.55 g, 1.31 mmol) and compound 40 (0.25 g, 0.873 mmol) in quinoline (9 mL) at room temperature was treated with silver oxide (0.40 g, 1.75 mmol) portionwise over 5 min. The resulting thick slurry was stirred for 30 min at room temperature and then triturated with hexanes (3×10 mL), decanting the supernatant. The viscous oil obtained was dissolved in CH$_2$Cl$_2$ (100 mL) and filtered through Celite. The filtrate was washed with saturated aq. NaHCO$_3$ (50 mL), dried (Na$_2$SO$_4$) and decolorized with Norit B to give 1.6 g of a red oil. The oil obtained was triturated with hexanes (3×50 mL), decanting the supernatant, to give 0.4 g of a pink-colored solid. Flash chromatography on silica gel (45% EtOAc/hexanes) gave 0.290 g (55%) of methyl 1-O-(4-[4-(methoxycarbonyl)phenylmethoxy)-2-formyl-phenyl)-2,3,4-tri-O-acetyl-β-D-glucopyranuranate as a cream-colored solid: mp 196.5–197.5° C.; R$_f$ 0.30 (50% EtOAc-hexanes); $^1$H NMR (300 MHz, CDCl$_3$) δ10.29 (s, 1H, CHO), 8.05 (d, 2H, J=8.2 Hz, H-3",5"), 7.48 (d, 2H, J=8.2 Hz, H-2",6"), 7.39 (d, 1H, J=3.0 Hz, H-3'), 7.19 (dd, J=3.0, 8.9 Hz, H-5'), 7.10 (d, J=8.9 Hz, H-6'), 5.4–5.26 (m, 3H, H-2,3,4), 5.18–5.05 (m, 3H, OCH$_2$ Ar, H-1), 4.16 (d, 1H, J=7.5 Hz, H-5), 3.92 (s, 3H, ArCO$_2$CH$_3$), 3.74 (s, 3H, CO$_2$CH$_3$), 2.08, 2.06, and 2.05 (3s, 9H, OAc); $^{13}$C NMR (75 MHz, CDCl$_3$) δ188.7, 169.9, 169.2, 169.0, 166.6, 166.5, 154.6, 153.2, 141.3, 129.9, 127.2, 127.0, 123.8, 118.8, 111.3, 99.9, 72.6, 71.5, 70.8, 69.8, 69.0, 53.1, 52.2, 20.6.

(2) A suspension of the compound prepared in (1) above (0.200 g, 0.332 mmol) in MeOH (3 mL) at 0° C. was treated with 10% aq NaOH (0.7 mL, 1.99 mmol) and allowed to stir and warm to room temperature over 8 h. The reaction mixture was neutralized to pH 7 with AcOH (~75 μL) and concentrated in vacuo. The disodium salt obtained was dissolved in water (5 mL) and acidified to pH 4 with 5% aq citric acid. The resulting precipitate was collected, washed with water (2×5 mL) and dried under high vacuum to give 0.090 g (58%) of 1-O-[4-(4-carboxyphenylmethoxy)-2-formyl-phenyl]-β-D-glucupyranosiduronic acid (4) as a cream-colored solid: mp 226–227° C. (dec); R$_f$ 0.40 (50:50:1, CHCl$_3$—MeOH—AcOH); $^1$H NMR (300 MHz, DMSO-d$_6$) δ10.42 (s, 1H, CHO), 7.95 (d, 2H, J=7.5 Hz, H-3",5"), 7.55 (d, 2H, J=7.5, H-2",6"), 7.45–7.15 (m, 3H, H-3',5',6'), 5.21 (s, 2H, OCH$_2$ Ar), 4.96 (d, 1H, J=4.8 Hz, H-1), 3.9–2.8 (m, H-2,3,4 and OH), 3.75 (d, 1H overlapping preceding multiplet, J=7.5 Hz, H-5); $^{13}$C NMR (75 MHz, DMSO-d$_6$) δ189.7, 170.4, 167.0, 154.2, 153.2, 141.7, 130.3, 129.4, 127.2, 125.7, 123.7, 118.9, 110.4, 101.6, 75.7, 74.8, 73.0, 71.5, 69.1.

Example 5

Preparation of 4-[(3-formyl-4-hydroxyphenoxy)methyl]benzoic acid (isotucaresol, compound III)

A suspension of compound 40 (0.50 g, 1.75 mmol) in a mixture of EtOH (5 mL) and 1N aq NaOH was stirred at room temperature for 2.5 h to give a light yellow solution. The reaction mixture was diluted with water (50 mL), washed with EtOAc (25 mL) and acidified with conc HCl (~1 mL). The off-white precipitate that formed was collected, washed with water, and dried under high vacuum to give 0.475 g (100%) of 4-[(3-formyl-4-hydroxyphenoxy)methyl]benzoic acid (isotucaresol; III) as a cream-colored powder: mp 222–224° C. (dec); R$_f$ 0.46 (10% MeOH-EtOAc); $^1$H NMR (300 MHz, acetone-d$_6$) δ10.62 (br s, 1 H, OH), 10.00 (s, 1H, CHO), 8.06 (d, 2H, J=8 Hz, H-2,6), 7.62 (d, 2H, J=8 Hz, H-3,5), 7.43 (d, 1H, J=3 Hz, H-2'), 7.33 (dd, J=3, 8.9 Hz, H-6'), 6.95 (d, 2H, J=8.9 Hz, H-5'), 2.44 (br s, 1H, OH); $^{13}$C NMR (75 MHz, acetone-d$_6$) δ197.2, 167.2, 156.7, 152.6, 143.3, 130.9, 130.6, 128.1, 126.5, 121.6, 119.1, 117.6, 70.7; HRMS calcd. for M+NH$_4$$^+$ 290.1028, found 290.1037; Anal. calcd. for C$_{15}$H$_{12}$O$_5$.0.25 H$_2$O: C, 65.09; H, 4.55. Found: C, 65.46; H, 4.56.

Example 6

Biological Evaluation

Hemolytic Activity

The hemolytic activities can be determined with an in vitro assay using sheep red blood cells (SRBC) according to a published procedure (Kensil et al., 1991). Since most Quillaja saponins cause hemolysis of SRBC in the range of 5 to 30 μg/ml, compounds (III), (IV–VI), and other compounds of the present invention are compared to commercially available Quil-A standard (Superfos) by serially diluting the test articles with PBS in 96-well round-bottom microtiter plates to final concentrations between 5 and 200 μg/ml. The final volume in each well is 100 μl. SRBC (40% sheep blood and 60% Alsever's solution) are washed three times by low speed centrifugation of the blood and resuspension of the pellet in PBS to 2.5 times the original volume. The resuspended cells (25 µl) are added to each well in the microtiter plate and mixed with the test article solutions. After incubation at room temperature for 30 min, the plates are centrifuged at 1000 rpm for 5 min to sediment unhemolyzed cells. Fifty µl of the supernatants are transferred to the wells of a flat-bottom microtiter plate. Absorbance caused by released hemoglobin is then determined at 570 nm.

Lethal Toxicity in Mice

Lethal toxicity of compounds (III), (IV–VI), and other compounds of the present invention are tested in CD-1 (ICR) mice in comparison to Quil A standard as previously described (Kensil et al., 1991). Groups of CD-1 mice (female, 8–10 wks) are injected intradermally with varying concentrations of the test articles in PBS and mortality is monitored for 72 h after injection. A control group of mice is injected with PBS only. The 50% lethal dose or $LD_{50}$ is calculated by the Reed-Muench method (see, Reed and Muench, *Am. J. Hygiene* 1938, 27: 493–497).

Murine Antibody and CTL Responses to rHBsAg

Groups of six BALB/c ($H-2^d$) female mice (5–6 wks) are immunized subcutaneously (inguinal region) or intranasally on day 0 and again on day 21 with 2.0 µg rHBsAg plus varying doses of compounds (III), (IV–VI), and other compounds of the present invention, or 2.0 µg alum-adsorbed rHBsAg (0.5 mg alum) plus compounds (III), (IV–VI), and other compounds of the present invention in PBS (200 µL/mouse s.c.; 20 µl/mouse i.n.). Control groups include nonimmune mice (no treatment) and mice receiving alum-adsorbed rHBsAg alone either s.c. or i.n. on days 0 and 21.

For the evaluation of antibody responses, serum and mucosal samples are collected 14 days after the second vaccination via the orbital plexus and by vaginal wash and individually tested for HBsAg-specific antibody activity by enzyme-linked immunosorbent assay (ELISA). The end-point antibody titers of each mouse are evaluated as total IgG, IgG1, IgG2a, IgG2b and IgA specific for rHBsAg.

The induction of cytotoxic T-lymphocyte response in the above immunized mice are determined by a cytotoxicity assay (see, Schirmbeck et al., *J. Immunol.* 1994, 152: 1110–1119; see, Schirmbeck et al., *J. Virol.* 1994, 68: 1418–1425). Fourteen days after the second injection single cell suspensions are prepared from splenic lymphocytes of 3 mice per group. The spleen cells ($75 \times 10^6$) are subsequently incubated at 37° C. in 10 ml RP10-SC media containing 50 nM of an $L^d$-restricted HBV CTL epitope (IPQSLDSWWTSL) for 4 days. Stimulated effector cells are harvested, resuspended to $5 \times 10^6$ cells/µl and serially diluted (in triplicate) in a volume of 100 µl RP10-SC/well of a 96 well microtiter plate followed by the addition of 100 ml of RP10-SC containing $1 \times 10^4$ $^{51}$Cr labeled P815S target cells (transfected P815 cells ($H-2^d$) expressing the hepatitis B S-antigen). Plates are centrifuged for 5 min at 400×g and placed in a 37° C. $CO_2$ incubator for 4 h. Percent specific cytotoxicity is then determined.

Murine Antibody Response to Formalin-inactivated Influenza and Protective Immune Responses to Infectious Influenza Influenza vaccines are formulated in PBS with one (1) hemagglutinating unit (HAU) of formalin-inactivated influenza A/HK/68 (FI-flu) and varying amounts of test articles (2, 4–6), except for the vehicle controls which contain no synthetic adjuvant. Groups of 10 BALB/c mice (female, 5–6 wks) are vaccinated either by subcutaneous injection at two distinct sites (100 µl/site) near the inguinal lymph nodes (total of 200 µL/mouse) or by intranasal administration (20 µl/mouse) on day 0 and again on day 21. Serum and mucosal samples are collected from mice (5 per group) 14 days after the second vaccination via the orbital plexus and by vaginal wash and then frozen at −70° C. until assessed by ELISA. The end-point influenza-specific antibody titers of each mouse are evaluated as total IgG, IgG1, IgG2a, IgG2b and IgA.

All mice immunized above are challenged 30 days post vaccination by i.n. administration of approximately 10 $LD_{50}$ infectious influenza A/HK/68. Mortality is assessed for 21 days following the challenge.

Example 7

Biological Evaluation of Isotucaresol (III) and with the AGP compound 99

Compound III, isotucaresol, was evaluated for adjuvant activity with a model hepatitis B vaccine. III, was prepared as an aqueous formulation in PBS and admixed with recombinant hepatitis B surface antigen (rHBsAg) (Rhein Biotech, Düsseldorf, Germany) with or without the AGP adjuvant 99 (2-[(R)-3-tetradecanoyloxytetradecanoylamino]ethyl 2-Deoxy-4-O-phosphono-3-O-[(R)-3-tetradecanoyloxy-tetradecanoyl]-2-[(R)-3-tetradecanoyloxytetradecanoyl-amino]-β-D-glucopyranoside Triethylammonium Salt). Mice were administered the vaccines on days 0 and 21 by subcutaneous (s.c.) injection of vaccine containing 1 µg rHBsAg±1000 µg III±5 µg 99. The antigen-specific immune response to rHBsAg was evaluated by measurement of serum antibody and cytotoxic T lymphocytes (CTL). The results shown in Table 1 indicate that III has adjuvant activity through its ability to mediate enhanced serum antibody production and acts synergistically with the AGP adjuvant 99.

TABLE 1

| Group[a] | Gross Geometric Mean Serum Titers[b,c] | | | |
| --- | --- | --- | --- | --- |
| | IgG | IgG1 | IgG2a | IgG2b |
| Nonimmune | 1X | 1X | 1X | 1X |
| rHBsAg + PBS | 500X | 500X | 100X | 8X |
| rHBsAg + III | 5,000X | 5,000X | 250X | 100X |
| rHBsAg + III + 99 | 20,000 | 5,000X | 15,000X | 5,000X |
| rHBsAg + 99 | 10,000X | 5,000X | 5,000X | 750X |

[a]Female BALB/c mice (8/group) were administered the vaccines on days 0 and 21 by subcutaneous (s.c.) injection of vaccine containing 1 µg rHBsAg ± 1000 µg III ± 5 µg 99.
[b]Serum from 5 mice/group was collected 21 days post-secondary vaccination and analyzed by ELISA.
[c]The symbol 1X = 0–100, 3X = 101–300, 5X = 301–500, 8X = 501–800, 10X = 801–1000, 15X = 1000–1500, 30X = 1500–3000, 100X = 3001–10,000, 150X = 10,001–15,000, 250X = 15,001–25,000, 500X = 25,001–50,000, 750X = 50,001–75,000, 1000X = 75,001–100,000, 5000X = 100,001–500,000, 10,000X = 500,001–1,000,000, 15,000X = 1,000,001–1,500,000, and 20,0000X = 1,500,001–2,000,000.

Spleen cells were collected from donor mice 26 days after the secondary vaccination and evaluated for CTL activity. rHBsAg directed specific lysis was assessed in a standard four hour $^{51}$Cr-release assay and by measurement of CD8+, IFNγ+ using flow cytometry. The results in Table 2 indicate that III enhances the CTL response to the vaccine antigen and has an additive effect to the adjuvant activity induced by 99.

TABLE 2

| Group[a] | Percent Specific Cell Lysis (50:1)[b,c] | Lymphocytes[d,e] CD8+, IFNγ+ |
|---|---|---|
| Nonimmune | − | N |
| rHBsAg + PBS | + | 2N |
| rHBsAg + III | 4+ | 2N |
| rHBsAg + III + 99 | 8+ | 4N |
| rHBsAg + 99 | 5+ | 3N |

[a]Female BALB/c mice (8/group) were administered the vaccines on days 0 and 21 by subcutaneous (s.c.) injection of vaccine containing 1 μg rHBsAg ± 1000 μg III ± 5 μg 99.
[b]The percent specific lysis is shown for cells suspended at a 50:1 effector:target ratio. Spleen cells were treated with Tris-buffered NH$_4$Cl to remove erythrocytes and resuspended at a concentration of 7.5 × 10$^6$/ml in RPMI/10% FCS supplemented with 5 mM Hepes, 4 mM L-glutamine, 0.05 mM 2-mercaptoethanol and antibiotics. A synthetic peptide representing a known MHC class I, L$^d$-restricted CTL epitope (IPQSLDSWWTSL) was added to the cells at a final concentration of 75 nM. After a four-day incubation, the cells were recovered and assessed for CTL activity. The target cells were a transfected P815 cell line (P815S), which express the Ld-restricted CTL epitope, or the non-transfected P815 cell line. In all cases lysis of the non transfected P815 cells was less than 10% at 50:1 effector:target ratio.
[c]The symbol "−" represents 0–2 Percent Specific Cell Lysis, "+" is 2–10 Percent Specific Cell Lysis, "2+" is 11–20 Percent Specific Cell Lysis, "3+" is 21–30 Percent Specific Cell Lysis, "4+" is 31–40 Percent Specific Cell Lysis, "5+" is 41–50 Percent Specific Cell Lysis, "6+" is 51–60 Percent Specific Cell Lysis, "7+" is 61–70 Percent Specific Cell Lysis, and "8+" is 71–80 Percent Specific Cell Lysis.
[d]A ratio of CD8+, IFNγ+ cells to total CD8+ cells is indicated. The CD8+, IFNγ+ cells represent antigen activated cells capable of inducing CTL activity. Spleen cells were treated with tris-buffered NH$_4$Cl to remove erythrocytes and resuspended in RPMI/10% FCS supplemented with 5 mM Hepes, 4 mM L-glutamine, 0.05 mM 2-mercaptoethanol and antibiotics. A synthetic peptide representing a known MHC class I, L$^d$-restricted CTL epitope (IPQSLDSWWTSL) was added to the cells at a final concentration of 75 nM. After a six-hour incubation the cells were stained for the CD8 cell-surface marker and the intracellular IFNγ with fluorescent-tagged monoclonal antibodies. The cells were evaluated by flow cytometry.
[e]The symbols, N, 1N, 2N, 3N, 4N, and 5N, represent the ranges of ratios of 1:5000–1:1000, 1:999–1:750, 1:749–1:500, 1:499–1:250, 1:249–1:200, and 1:199–1:100, respectively.

Example 8

Bioloaical Evaluation of compounds 40, 42, and 44 with compound 99

Compounds 40, 42, and 44, were evaluated for adjuvant activity with a model hepatitis B vaccine. These compounds were prepared as aqueous formulations in PBS and admixed with recombinant hepatitis B surface antigen (rHBsAg) with or without the AGP adjuvant 99. Compound 99 was solubilized in an aqueous formulation containing dipalmitoylphosphatidyl choline in water. Mice were administered the vaccines on days 0 and 14 by subcutaneous (s.c.) injection. The mouse dose for each vaccine is given in table 3. The antigen-specific immune response to rHBsAg was evaluated by measurement of serum antibody and cytotoxic T lymphocytes (CTL). The results shown in Table 3 confirm the adjuvant activity of compounds of 40, 42, and 44. Each molecule mediated enhanced serum antibody production.

TABLE 3

| Group[a] | Adjuvant Dose (μg) | Gross Geometric Serum Titers[b,c] | | | |
|---|---|---|---|---|---|
| | | IGG | IgG1 | IgG2a | IgG2b |
| Nonimmune | — | 1X | 1X | 1X | 1X |
| rHBsAg/PBS | — | 100X | 150X | 3X | 3X |
| rHBsAg/40 | 1000 | 750X | 5,000X | 100X | 15X |
| rHBsAg/40 | 500 | 500X | 5,000X | 30X | 15X |
| rHBsAg/40 + 99 | 500/5 | 5,000X | 750X | 5,000X | 500X |
| rHBsAg/40 | 250 | 500X | 1,000X | 250X | 30X |
| rHBsAg/42 | 1000 | 100X | 500X | 8X | 8X |
| rHBsAg/42 | 500 | 100X | 150X | 15X | 8X |
| rHBsAg/42 + 99 | 500/5 | 5,000X | 5,000X | 750X | 15X |
| rHBsAg/42 | 250 | 30X | 1,000X | 30X | 8X |
| rHBsAg/44 | 1000 | 100X | 15X | 15X | 10X |
| rHBsAg/44 | 500 | 100X | 30X | 15X | 10X |
| rHBsAg/44 + 99 | 500/5 | 5,000X | 500X | 5,000X | 500X |
| rHBsAg/44 | 250 | 15X | 500X | 15X | 10X |
| rHBsAg/99 | 5 | 5,000X | 750X | 5,000X | 500X |

[a]Female BALB/c mice (8/group) were administered the vaccines on days 0 and 14 by subcutaneous (s.c.) injection of vaccine.
[b]Serum from 5 mice/group was collected 11 days post-secondary vaccination and analyzed by ELISA.
[c]The symbol 1X = 0–100, 3X = 101–300, 5X = 301–500, 8X = 501–800, 10X = 801–1000, 15X = 1000–1500, 30X = 1500–3000, 100X = 3001–10,000, 150X = 10,001–15,000, 250X = 15,001–25,000, 500X = 25,001–50,000, 750X = 50,001–75,000, 1000X = 75,001–100,000, 5000X = 100,001–500,000, 10,000X = 500,001–1,000,000, 15,000X = 1,000,001–1,500,000, and 20,0000X = 1,500,001–2,000,000.

Spleen cells were collected from donor mice 11 days after the secondary vaccination and evaluated for CTL activity. The rHBsAg directed CTL was assessed by measurement of CD8+, IFNγ+ using flow cytometry. The results in Table 4 indicate that compounds 40, 42, and 44 enhance the CTL response to the hepatitis vaccine antigen.

TABLE 4

| Group[a] | ADJUVANT Dose (μg) | CTL Ratio of CD8+, IFNγ+ Lymphocytes[b,c] |
|---|---|---|
| Nonimmmune | — | N |
| rHBsAg/PBS | — | 3N |
| rHBsAg/40 | 1000 | 5N |
| rHBsAg/40 | 500 | 2N |
| rHBsAg/40 + 99 | 500/5 | 5N |
| rHBsAg/40 | 250 | 3N |
| rHBsAg/42 | 1000 | 2N |
| rHBsAg/42 | 500 | 3N |
| rHBsAg/42 + 99 | 500/5 | 5N |
| rHBsAg/42 | 250 | 5N |
| rHBsAg/44 | 1000 | 2N |
| rHBsAg/44 | 500 | 3N |
| rHBsAg/44 + 99 | 500/5 | 3N |
| rHBsAg/44 | 250 | 4N |
| rHBsAg/99 | 5 | 4N |

[a]Female BALB/c mice (6–7/group) were administered the vaccines on days 0 and 14 by subcutaneous (s.c.) injection of vaccine.
[b]A ratio of CD8+, IFNγ+ cells to total CD8+ cells is indicated. The CD8+, IFNγ+ cells represent antigen activated cells capable of inducing CTL activity. Spleen cells were treated with tris-buffered NH$_4$Cl to remove erythrocytes and resuspended in RPMI/10% FCS supplemented with 5 mM Hepes, 4 mM L-glutamine, 0.05 mM 2-mercaptoethanol and antibiotics. A synthetic peptide representing a known MHC class I, L$^d$-restricted CTL epitope (IPQSLDSWWTSL) was added to the cells at a final concentration of 75 nM. After a six-hour incubation the cells were stained for the CD8 cell-surface marker and the intracellular IFNγ with fluorescent-tagged monoclonal antibodies. The cells were evaluated by flow cytometry.
[c]The symbols, N, 1N, 2N, 3N, 4N, and 5N, represent the ranges of ratios of 1:5000–1:1000, 1:999–1:750, 1:749–1:500, 1:499–1:250, 1:249–1:200, and 1:199–1:100, respectively.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound, having the formula:

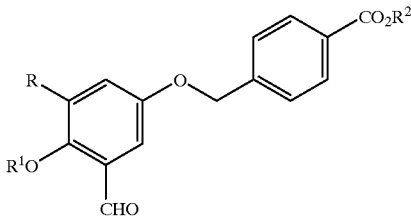

wherein, R is hydrogen or —C(O)H; $R^1$ is a member selected from the group consisting of hydrogen, a substituted $C_{1-20}$ saturated, unsaturated or cyclic alkyl, saturated or unsaturated heteroalkyl or saturated or unsaturated heterocycloalkyl group, an unsubstituted $C_{1-20}$ saturated, unsaturated or cyclic alkyl, saturated or unsaturated heteroalkyl or saturated or unsaturated heterocycloalkyl group, a saccharyl group, and a group represented by the formula —C(O)—[C($R^3$)($R^4$)]$_n$—COOH, wherein each $R^3$ and $R^4$ independently is a member selected from the group consisting of hydrogen and a substituted $C_{1-10}$ saturated, unsaturated or cyclic alkyl, saturated or unsaturated heteroalkyl or saturated or unsaturated heterocycloalkyl group, and an unsubstituted $C_{1-10}$ saturated, unsaturated or cyclic alkyl, saturated or unsaturated heteroalkyl or saturated or unsaturated heterocycloalkyl group; and n is a number from 1 to 5; $R^2$ is a member selected from the group consisting of hydrogen, a substituted $C_{1-20}$ saturated unsaturated or cyclic alkyl, saturated or unsaturated heteroalkyl or saturated or unsaturated heterocycloalkyl group, an unsubstituted $C_{1-20}$ saturated unsaturated or cyclic alkyl, saturated or unsaturated heteroalkyl or saturated or unsaturated heterocycloalkyl group, and a group represented by the formula —(CH$_2$)$_m$CH(OH)(CH$_2$)$_p$OR$^5$, wherein m and p are independently 1 or 2, and $R^5$ is a substituted $C_{2-20}$ saturated, unsaturated or cyclic alkyl, saturated or unsaturated heteroalkyl or saturated or unsaturated heterocycloalkyl group, or an unsubstituted $C_{2-20}$ saturated, unsaturated or cyclic alkyl, saturated or unsaturated heteroalkyl or unsaturated heterocycloalkyl group, or a group represented by the formula

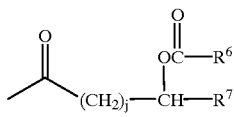

wherein j is 1–5, and $R^6$ and $R^7$ are independently selected from the group consisting of hydrogen, a substituted $C_{1-20}$ saturated, unsaturated or cyclic alkyl, saturated or unsaturated heteroalkyl or saturated or unsaturated heterocycloalkyl group, and an unsubstituted $C_{1-20}$ saturated, unsaturated or cyclic alkyl, saturated or unsaturated heteroalkyl or saturated or unsaturated heterocycloalkyl group;

or a pharmacologically acceptable salt thereof.

2. The compound of claim 1 wherein the saccharyl group is a mono- or disaccharide.

3. The compound of claim 1 wherein the saccharyl group is a glucuronic acid group.

4. The compound of claim 1 wherein R, $R^1$, and $R^2$ are hydrogens.

5. The compound of claim 1 wherein R is hydrogen; $R^1$ is a saccharyl group, wherein the saccharyl group is a glucuronic acid group; and $R^2$ is hydrogen.

6. The compound of claim 5 wherein the glucuronic acid group is a β-D-glucuronic acid group.

7. The compound of claim 1 wherein R is hydrogen; $R^1$ is represented by the formula —C(O)—[C($R^3$)($R^4$)]$_n$—COOH wherein $R^3$ and $R^4$ are hydrogens and n is 2; and $R^2$ is hydrogen.

8. The compound of claim 1 wherein R is hydrogen; $R^1$ is a saccharyl group, wherein the saccharyl group is a glucuronic acid group; and $R^2$ is (CH$_2$)$_m$CH(OH)(CH$_2$)$_m$OR$^5$, wherein m is 1, and $R^5$ is a substituted $C_{2-20}$ acyl group, or an unsubstituted $C_{2-20}$ acyl group.

9. The compound of claim 8 wherein (CH$_2$)$_m$CH(OH)(CH$_2$)$_m$OR$^5$ is a 1-O-acyl-sn-glyceryl group.

10. The compound of claim 9 wherein the acyl group is a member selected from the group consisting of an acetyl group, an octanoyl group, and a tetradecanoyl group.

11. The compound of claim 1 wherein R is hydrogen; $R^1$ is a saccharyl group, wherein the saccharyl group is a glucuronic acid group; and $R^2$ is a group represented by the formula

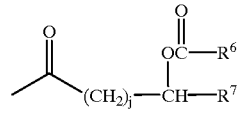

wherein j is 1; $R^6$ is a substituted $C_{1-20}$ saturated, unsaturated or cyclic alkyl, saturated or unsaturated heteroalkyl or saturated or unsaturated heterocycloalkyl group, or an unsubstituted $C_{1-20}$ saturated, unsaturated or cyclic alkyl, saturated or unsaturated heteroalkyl or saturated or unsaturated heterocycloalkyl group; and $R^7$ is a substituted $C_{1-20}$ saturated, unsaturated or cyclic alkyl, saturated or unsaturated heteroalkyl or saturated or unsaturated heterocycloalkyl group, or an unsubstituted $C_{1-20}$ saturated, unsaturated or cyclic alkyl, saturated or unsaturated heteroalkyl or saturated or unsaturated heterocycloalkyl group.

12. The compound of claim 11 wherein $R^7$ is a substituted $C_{11}$ saturated, unsaturated or cyclic alkyl, saturated or unsaturated heteroalkyl or saturated or unsaturated heterocycloalkyl group, or an unsubstituted $C_{11}$ saturated, unsaturated or cyclic alkyl, saturated or unsaturated heteroalkyl or saturated or unsaturated heterocycloalkyl group.

13. The compound of claim 1, wherein $R^1$ is a group having the formula

—(CH$_2$)$_x$COOR$^8$, wherein $R^8$ is hydrogen, a substituted $C_{1-20}$ saturated, unsaturated or cyclic alkyl, saturated or unsaturated heteroalkyl or unsaturated heterocycloalkyl group, or an unsubstituted $C_{1-20}$ saturated, unsaturated or cyclic alkyl, saturated or unsaturated heteroalkyl or unsaturated heterocycloalkyl group, wherein X is an integer from 1 to 7.

14. The compound of claim 13, wherein X is an integer from 2 to 4.

15. A liposome vesicle comprising the compound of claim 1.

16. A vaccine composition comprising an antigen and the compound of claim 1.

17. The vaccine composition of claim 16 wherein the antigen is a bacterial antigen.

18. The vaccine composition of claim 16 wherein the antigen is a viral antigen.

19. The vaccine composition of claim 16 wherein the antigen is a tumor associated antigen.

20. The vaccine composition of claim 16 wherein the antigen is a self-antigen.

21. An adjuvant composition for potentiating the immunogenicity of an antigen, comprising a suspension of water or an aqueous solution, wherein said suspension or solution comprises the compound of claim 1.

22. The adjuvant composition of claim 21 wherein the suspension is an oil-in-water emulsion.

23. The adjuvant composition of claim 19 wherein the suspension is a water-in-oil emulsion.

24. The adjuvant composition of claim 21 wherein the suspension is a micellar dispersion comprising at least one surfactant.

25. The adjuvant composition of claim 24 wherein the surfactant comprises dipalmitoyl phosphatidylcholine (DPPC).

26. A method for inducing or enhancing immunogenicity of an antigen in a mammal, comprising administering to said mammal a vaccine composition comprising the antigen and a vaccine adjuvant composition comprising an effective immunopotentiatory amount of the compound of claim 1.

27. The method of claim 26 wherein said vaccine composition is administered orally, topically, epicutaneously, intramuscularly, intradermally, subcutaneously, intranasally, intravaginally, sublingually, or via inhalation.

* * * * *